(12) United States Patent
Tortonese et al.

(10) Patent No.: US 9,211,403 B2
(45) Date of Patent: Dec. 15, 2015

(54) STEERABLE STYLET

(75) Inventors: Marco Tortonese, Mountain View, CA (US); Timothy Beerling, San Francisco, CA (US); Matthew I. Haller, Valley Village, CA (US)

(73) Assignee: ADVANCED BIONICS, LLC, Valencia, CA (US)

( * ) Notice: Subject to any disclaimer, the term of this patent is extended or adjusted under 35 U.S.C. 154(b) by 1412 days.

(21) Appl. No.: 12/915,375

(22) Filed: Oct. 29, 2010

(65) Prior Publication Data

US 2011/0106101 A1 May 5, 2011

Related U.S. Application Data

(60) Provisional application No. 61/256,847, filed on Oct. 30, 2009.

(51) Int. Cl.
*A61N 1/05* (2006.01)
*A61M 25/01* (2006.01)
*A61N 1/08* (2006.01)

(52) U.S. Cl.
CPC .......... *A61N 1/0541* (2013.01); *A61M 25/0102* (2013.01); *A61M 25/0147* (2013.01); *A61N 1/08* (2013.01)

(58) Field of Classification Search
CPC ........... A61B 19/201; A61B 2019/208; A61B 17/3468; A61B 2019/465; A61N 1/056; A61N 1/0541; A61N 1/0587; A61N 1/36032; A61N 2001/0578; A61F 2/18; A61F 2002/183; A61M 25/01; A61M 25/0102; A61M 25/0147; A61M 2025/0036
USPC ..................... 606/108, 129; 623/10; 607/137
See application file for complete search history.

(56) References Cited

U.S. PATENT DOCUMENTS

| 3,751,605 | A | 8/1973 | Michelson |
| 4,400,590 | A | 8/1983 | Michelson |
| 4,865,037 | A | 9/1989 | Chin et al. |
| 4,940,050 | A | 7/1990 | Forssmann et al. |
| 5,045,662 | A | 9/1991 | Yamada |
| 5,300,106 | A | 4/1994 | Dahl et al. |
| 5,396,902 | A * | 3/1995 | Brennen et al. ............ 600/585 |

(Continued)

FOREIGN PATENT DOCUMENTS

| DE | 102010027692 | 10/2012 |
| EP | 1754509 B1 | 6/2009 |
| EP | 2113283 A1 | 11/2009 |
| WO | 9414494 A2 | 7/1994 |
| WO | 0032105 | 6/2000 |

(Continued)

OTHER PUBLICATIONS

Tanimoto et al., Apr. 1997, "Micro Force Sensor for Invtravascular Nuerosurgery", Robotics and Automation, vol. 2, pp. 1561-1566.*

(Continued)

*Primary Examiner* — Katherine Rodjom
*Assistant Examiner* — Christian Knauss
(74) *Attorney, Agent, or Firm* — Steven L. Nichols; Fabian VanCott

(57) ABSTRACT

A stylet for inserting an electrode array into a cochlea includes a first sensor insertable within a lumen of the electrode array and sensitive to force applied by a lumen wall to the first sensor and a first actuator adapted to move the electrode array in response to the force sensed by the first sensor.

5 Claims, 16 Drawing Sheets

(56) References Cited

U.S. PATENT DOCUMENTS

| | | | |
|---|---|---|---|
| 5,443,493 A | 8/1995 | Byers et al. | |
| 5,469,840 A | 11/1995 | Tanii et al. | |
| 5,507,725 A | 4/1996 | Savage et al. | |
| 5,545,219 A * | 8/1996 | Kuzma | 623/10 |
| 5,623,582 A | 4/1997 | Rosenberg | |
| 5,626,629 A | 5/1997 | Faltys et al. | |
| 5,628,629 A | 5/1997 | Mitani et al. | |
| 5,771,902 A | 6/1998 | Lee et al. | |
| 5,784,542 A | 7/1998 | Ohm et al. | |
| 5,876,373 A | 3/1999 | Giba et al. | |
| 5,938,691 A | 8/1999 | Schulman et al. | |
| 5,964,714 A | 10/1999 | Lafontaine | |
| 6,038,484 A | 3/2000 | Kuzma | |
| 6,067,474 A | 5/2000 | Schulman et al. | |
| 6,070,105 A | 5/2000 | Kuzma | |
| 6,077,244 A | 6/2000 | Botich et al. | |
| 6,096,004 A | 8/2000 | Meglan et al. | |
| 6,112,124 A | 8/2000 | Loeb | |
| 6,112,598 A | 9/2000 | Tenerz et al. | |
| 6,119,044 A * | 9/2000 | Kuzma | 607/137 |
| 6,125,302 A | 9/2000 | Kuzma | |
| 6,129,753 A | 10/2000 | Kuzma | |
| 6,144,883 A | 11/2000 | Kuzma | |
| 6,157,861 A | 12/2000 | Faltys et al. | |
| 6,163,729 A * | 12/2000 | Kuzma | 607/137 |
| 6,167,763 B1 | 1/2001 | Tenerz et al. | |
| 6,203,485 B1 | 3/2001 | Urick | |
| 6,210,346 B1 * | 4/2001 | Hall et al. | 600/561 |
| 6,249,704 B1 | 6/2001 | Maltan et al. | |
| 6,272,371 B1 * | 8/2001 | Shlomo | 600/424 |
| 6,289,247 B1 | 9/2001 | Faltys et al. | |
| 6,358,281 B1 | 3/2002 | Berrang et al. | |
| 6,390,970 B1 | 5/2002 | Muller | |
| 6,421,569 B1 * | 7/2002 | Treaba et al. | 607/137 |
| 6,493,573 B1 | 12/2002 | Martinelli et al. | |
| 6,619,044 B2 | 9/2003 | Batchelor et al. | |
| 6,671,550 B2 | 12/2003 | Iaizzo et al. | |
| 6,741,878 B2 * | 5/2004 | Fuimaono et al. | 600/374 |
| 6,748,255 B2 | 6/2004 | Fuimaono et al. | |
| 6,970,730 B2 | 11/2005 | Fuimaono et al. | |
| 6,973,340 B2 | 12/2005 | Fuimaono et al. | |
| 6,976,965 B2 | 12/2005 | Corl et al. | |
| 7,097,620 B2 | 8/2006 | Corl et al. | |
| 7,153,299 B1 * | 12/2006 | Tu et al. | 606/15 |
| 7,257,434 B2 | 8/2007 | Fuimaono et al. | |
| 7,449,002 B1 | 11/2008 | Wenstad | |
| 7,472,601 B1 | 1/2009 | Tenerz et al. | |
| 8,260,437 B2 | 9/2012 | Llinas et al. | |
| 2001/0031909 A1 * | 10/2001 | Faltys et al. | 600/25 |
| 2001/0049466 A1 | 12/2001 | Leysieffer et al. | |
| 2002/0012438 A1 | 1/2002 | Leysieffer et al. | |
| 2002/0032391 A1 | 3/2002 | McFann et al. | |
| 2002/0042632 A1 | 4/2002 | Iaizzo et al. | |
| 2002/0103446 A1 | 8/2002 | McFann et al. | |
| 2002/0161114 A1 | 10/2002 | Gunatillake et al. | |
| 2002/0173799 A1 | 11/2002 | Besharim et al. | |
| 2003/0040684 A1 | 2/2003 | Soukup et al. | |
| 2003/0159518 A1 | 8/2003 | Sawatari et al. | |
| 2003/0171758 A1 * | 9/2003 | Gibson et al. | 606/129 |
| 2004/0097965 A1 * | 5/2004 | Gardeski et al. | 606/129 |
| 2004/0122360 A1 * | 6/2004 | Waldhauser et al. | 604/95.04 |
| 2004/0138562 A1 * | 7/2004 | Makower et al. | 600/439 |
| 2005/0085715 A1 | 4/2005 | Dukesherer et al. | |
| 2005/0085720 A1 | 4/2005 | Jascob et al. | |
| 2005/0171508 A1 | 8/2005 | Gilboa | |
| 2005/0234535 A1 | 10/2005 | Risi et al. | |
| 2005/0268724 A1 | 12/2005 | Tenerz | |
| 2006/0089569 A1 | 4/2006 | Soukup et al. | |
| 2006/0094982 A1 | 5/2006 | Corl et al. | |
| 2006/0133715 A1 * | 6/2006 | Belleville et al. | 385/13 |
| 2006/0167472 A1 * | 7/2006 | Hong et al. | 606/129 |
| 2006/0235314 A1 * | 10/2006 | Migliuolo et al. | 600/505 |
| 2006/0235500 A1 * | 10/2006 | Gibson et al. | 607/137 |
| 2006/0241505 A1 * | 10/2006 | Ahmed et al. | 600/486 |
| 2006/0293643 A1 | 12/2006 | Wallace et al. | |
| 2007/0016067 A1 | 1/2007 | Webster et al. | |
| 2007/0060847 A1 * | 3/2007 | Leo et al. | 600/587 |
| 2007/0123764 A1 * | 5/2007 | Thao et al. | 600/374 |
| 2007/0197896 A1 | 8/2007 | Moll et al. | |
| 2007/0225787 A1 * | 9/2007 | Simaan et al. | 607/137 |
| 2008/0009750 A1 * | 1/2008 | Aeby et al. | 600/478 |
| 2008/0015568 A1 * | 1/2008 | Paul et al. | 606/41 |
| 2008/0077049 A1 | 3/2008 | Hirshman | |
| 2008/0127065 A1 | 5/2008 | Bryant et al. | |
| 2008/0147173 A1 | 6/2008 | Mciff et al. | |
| 2008/0154339 A1 | 6/2008 | Carter | |
| 2008/0200928 A1 | 8/2008 | Savall Calvo et al. | |
| 2008/0275442 A1 * | 11/2008 | Paul et al. | 606/41 |
| 2008/0285909 A1 * | 11/2008 | Younge et al. | 385/13 |
| 2009/0012422 A1 | 1/2009 | Marban | |
| 2009/0088650 A1 | 4/2009 | Corl | |
| 2009/0259140 A1 | 10/2009 | Buchman et al. | |
| 2009/0275818 A1 * | 11/2009 | Rau et al. | 600/379 |
| 2009/0287092 A1 * | 11/2009 | Leo et al. | 600/474 |
| 2009/0312769 A1 * | 12/2009 | Dadd et al. | 606/129 |
| 2010/0049318 A1 | 2/2010 | Jolly et al. | |
| 2010/0063478 A1 * | 3/2010 | Selkee | 604/524 |
| 2010/0094311 A1 | 4/2010 | Jolly et al. | |
| 2010/0114288 A1 | 5/2010 | Haller et al. | |
| 2010/0125311 A1 | 5/2010 | Choi et al. | |
| 2011/0066160 A1 * | 3/2011 | Simaan et al. | 606/129 |
| 2011/0098719 A1 * | 4/2011 | Llinas et al. | 606/129 |
| 2011/0137393 A1 * | 6/2011 | Pawsey et al. | 607/137 |
| 2011/0319913 A1 | 12/2011 | Labadie et al. | |
| 2012/0071890 A1 | 3/2012 | Taylor et al. | |
| 2012/0083713 A1 | 4/2012 | Creighton et al. | |
| 2012/0172893 A1 | 7/2012 | Taylor et al. | |
| 2013/0138117 A1 | 5/2013 | Abbott et al. | |
| 2013/0172901 A1 | 7/2013 | Bozorg Grayeli et al. | |
| 2014/0350640 A1 | 11/2014 | Patrick et al. | |

FOREIGN PATENT DOCUMENTS

| | | |
|---|---|---|
| WO | 0126734 A1 | 4/2001 |
| WO | 0180922 A2 | 11/2001 |
| WO | 0180922 A3 | 11/2001 |
| WO | 03049658 A1 | 6/2003 |
| WO | 2004045363 A2 | 6/2004 |
| WO | 2004045363 A3 | 6/2004 |
| WO | 2005004760 A1 | 1/2005 |
| WO | 2005009215 A2 | 2/2005 |
| WO | 2005084122 A2 | 9/2005 |
| WO | 2005084122 A3 | 9/2005 |
| WO | 2006027781 A2 | 3/2006 |
| WO | 2006027781 A3 | 3/2006 |
| WO | 2006048097 A1 | 5/2006 |
| WO | 2006118915 A2 | 11/2006 |
| WO | 2006118915 A3 | 10/2007 |
| WO | 2009070616 A2 | 6/2009 |
| WO | 2009124287 A1 | 10/2009 |
| WO | 2009070616 A3 | 1/2010 |
| WO | 2010042611 A1 | 4/2010 |
| WO | 20100053673 A2 | 5/2010 |
| WO | 2010053673 A3 | 7/2010 |
| WO | 2011053766 A1 | 5/2011 |
| WO | 2011103059 | 8/2011 |
| WO | 2012010783 A1 | 1/2012 |
| WO | 2012040297 A2 | 3/2012 |
| WO | 2012040297 A3 | 3/2012 |
| WO | 2012040355 A2 | 3/2012 |
| WO | 2012040355 A3 | 6/2012 |
| WO | 2012168921 A2 | 12/2012 |
| WO | 2013038363 A2 | 3/2013 |
| WO | 2013071367 A1 | 5/2013 |
| WO | 2013166293 A1 | 11/2013 |

OTHER PUBLICATIONS

Schurzig et al., "A Force Sensing Automated Insertion Tool for Cochlear Electrode implantation," 2010 IEEE International Conference on Robotics and Automation Anchorage Convention District May 3-8, 2010, Anchorage, Alaska, USA.

(56) References Cited

OTHER PUBLICATIONS

Johnson; Microfabrication of Biocompatible Stimulation Electrode Arrays for Cochlear Implants; 24th Annual Microelectronic Engineering Conference, May 2006.

Wise et al; Microelectrodes, Microelectronics, and Implantable Neural Microsystems; Proceedings of the IEEE, vol. 96, No. 7, p. 1184-1202, Jul. 2008.

Bell et al; A Flexible micromachined electrode array for a cochlear prosthesis,; Sensors and Actuators. A Physical Transducers '97: International Conference on Solid-State Sensors and Actuators No. 9, 1998, vol. 66, Abstract.

Specialty Photonics; ClearLite Micro 980 Photonic Fiber; Specialty Single-Mode Fiber Specification Sheet; www.specialtyphotonics.com.

Dr. Rüdiger Paschotta; Encyclopedia of Laser Physics and Technology, Bend Losses; Nov. 11, 2008.

RP Photonics; Encyclopedia of Laser Physics and Technology, Bend Losses; www.rp-photonics.com/bend_losses.html.

Pennwell, Laserfocusworld; Fiber Fabrication: Single-mode Fiber has very low bending loss; www.optoiq.com/index/photonics-technologies-applications.

Wikipedia, The Free Encyclopedia; Fused Quartz; http://en.wikipedia.org/wiki/Fused_quartz.

Bhatti et al; ISSCC 2006/Session 2/Biomedical Systems/ 2.3; A 32 Site 4-Channel Cochlear Electrode Array; 2006 IEEE International Solid-State Circuits Conference; University of Michigan, Ann Arbor, MI.

Wang et al; An Integrated Position-Sensing System for a Mems-Based Cochlear Implant; Engineering Research Center for Wireless Integrated MicroSystems; Department of Electrical Engineering and Computer Science, University of Michigan; 2009.

Wang et al; A Hybrid Electrode Array with Built-In Position Sensors for an Implantable MEMS-Based Cochlear Prosthesis; IEEE Xplore; University of California Berkeley; 2009.

Chorost; Making Deaf Ears Hear with Light, A laser-based approach could make cochlear implants, which currently use electrical signals, more effective; www.technologyreview.com; Aug. 10, 2007.

Adunka et al; Monitoring of Cochlear Function During Cochlear Implantation; Laryngoscope 116: Jun. 2008, 1017-1255.

Polymicro Technologies; Mechanical Stress and Fiber Strength; www.polymicro.com/catalog/2_25.html.

Technica S.A.; Fiber Bragg Grating Sensor; www.technicasa.com.

Wise et al; High-Density Cochlear Implants with Position sensing and control; www.elsevier.com/locate/heares; Hearing Research 242 (2008) 22-30.

Wise et al; Wireless Implantable Microsystems: High-Density Electronic Interfaces to the Nervous System; Proceedings of the IEEE, vol. 92, No. 1, Jan. 2004.

REFDOC.FR; A flexible micromachined electrode array for a cochlear prosthesis; http://cat.inist.fr/?aModele=afficheN&cpsidt=2254424.

http://www.micronoptics.com/SENSORS_PRODUCTS.

Thomas Roland Jr, "A Model for Cochlear Implant Electrode Insertion and Force Evaluation: Results with a New Electrode Design and Insertion Technique," The Laryngoscope, 115, Aug. 2005, pp. 1325-1339.

"Medic Vision Ltd Utilizes SensAble Technologies' Haptic Devices to Deliver Realistic Surgical Drilling Training: Touch-enabled Simulators Provide Unlimited Practice for Better ENT Specialist Training, Improved Patient Outcomes and Safety," May 7, 2008, http://www.prweb.com/releases/sensable/medic_vision/prweb924954.htm.

"Cochlear Implant Electrode Design and Preservation of Residual Hearing," Andreas Jäger et al., Feb. 2, 2008 http://www.medel.com.ar/ENG/US/50_Resources/30_Conference_presentations/30_Manchester_Sept_2002/110_manchester_residual.asp.

Catherine A. Todd et al., "Force Application During Cochlear Implant Insertion: An Analysis for Improvement of Surgeon Technique," IEEE Transactions on Biomedical Engineering, vol. 54, No. 7, Jul. 2007, pp. 1247-1255.

Kurt E. Petersen, Proc IEEE, vol. 70, 420 (1982) http://www-inst.eecs.berkeley.edu/~n245/fa01/PETERSEN.PDF.

* cited by examiner

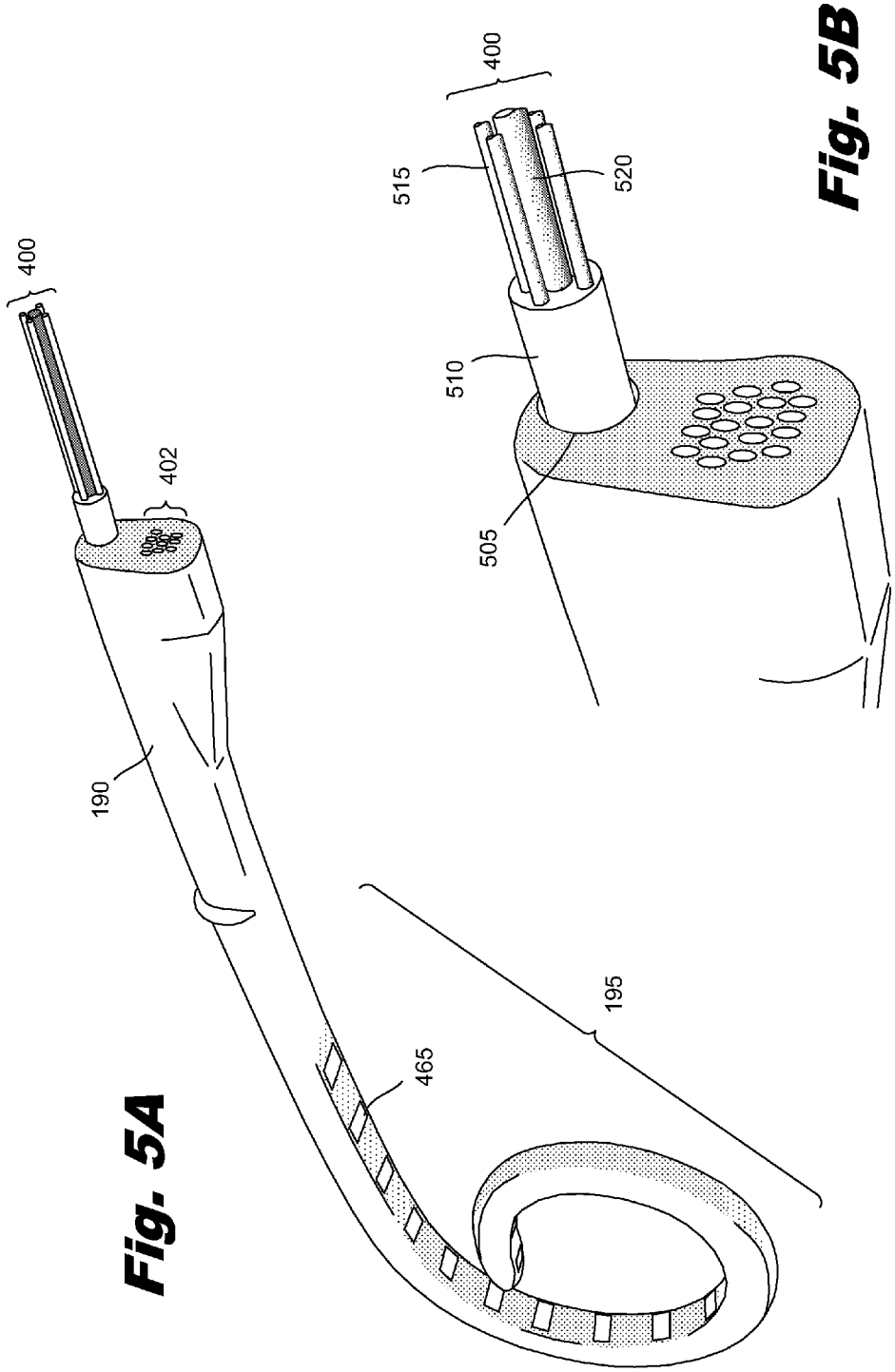

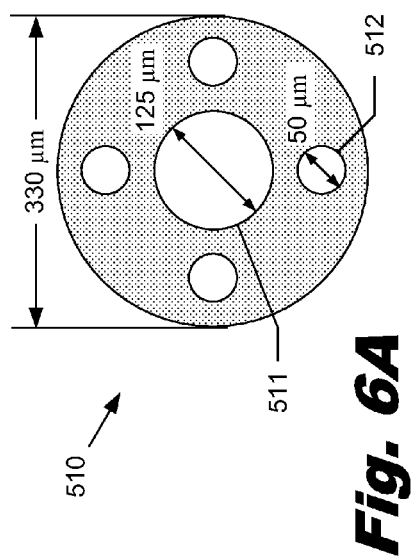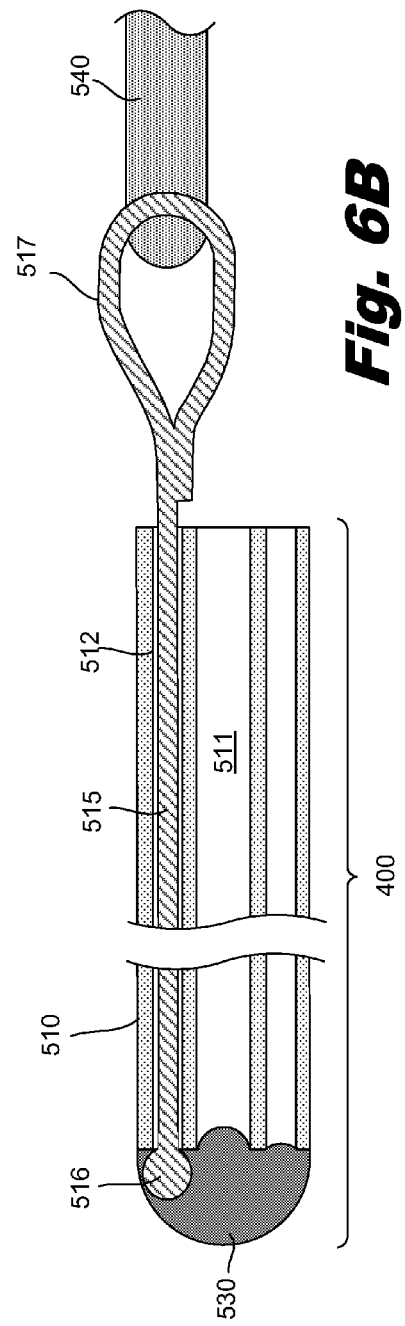

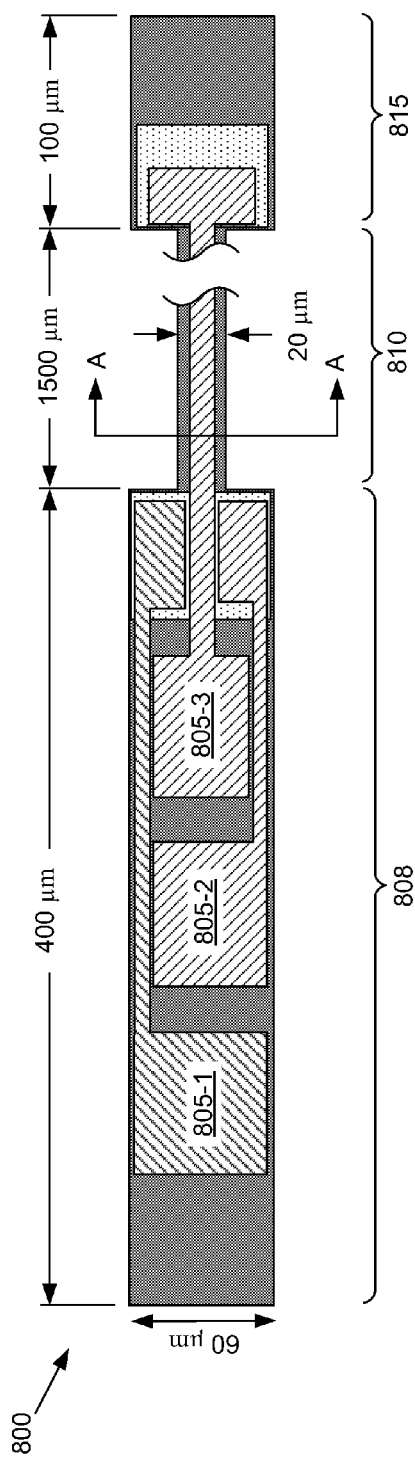
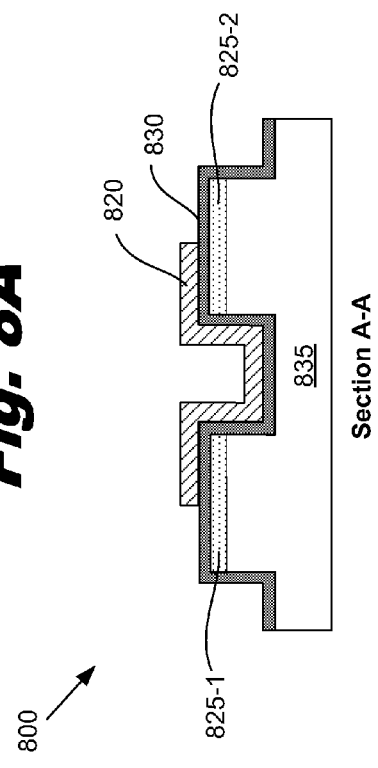
Fig. 8A
Fig. 8B
Section A-A

STEERABLE STYLET

RELATED DOCUMENTS

The present application claims the benefit under 35 U.S.C. §119(e) of U.S. Provisional Application No. 61/256,847, entitled "Cochlear Implant Insertion Device" filed Oct. 30, 2009, which is incorporated herein by reference in its entirety.

BACKGROUND

Reducing trauma to the cochlea due to implantation of a cochlear implant is desirable to improve the chance of preserving residual hearing, particularly for electric-acoustic stimulation (EAS), improved music appreciation, hearing in noise, and overall patient performance. Trauma to the cochlea can occur when the electrode array contacts the delicate internal tissues of the cochlea during insertion. This contact can damage these tissues and electrode array to loss of residual hearing.

BRIEF DESCRIPTION OF THE DRAWINGS

The accompanying drawings illustrate various embodiments of the principles described herein and are a part of the specification. The illustrated embodiments are merely examples and do not limit the scope of the claims.

FIGS. 5A and 5B are perspective views of an illustrative electrode array with a steerable stylet, according to one example of principles described herein.

FIG. 6A is a cross sectional diagram of a multi-lumen tube, according to one example of principles described herein.

FIG. 6B is a cross sectional diagram of a steerable stylet, according to one example of principles described herein.

FIGS. 8A and 8B are diagrams of an illustrative silicon strain gage, according to one example of principles described herein.

Throughout the drawings, identical reference numbers designate similar, but not necessarily identical, elements.

DETAILED DESCRIPTION

Figure 1:
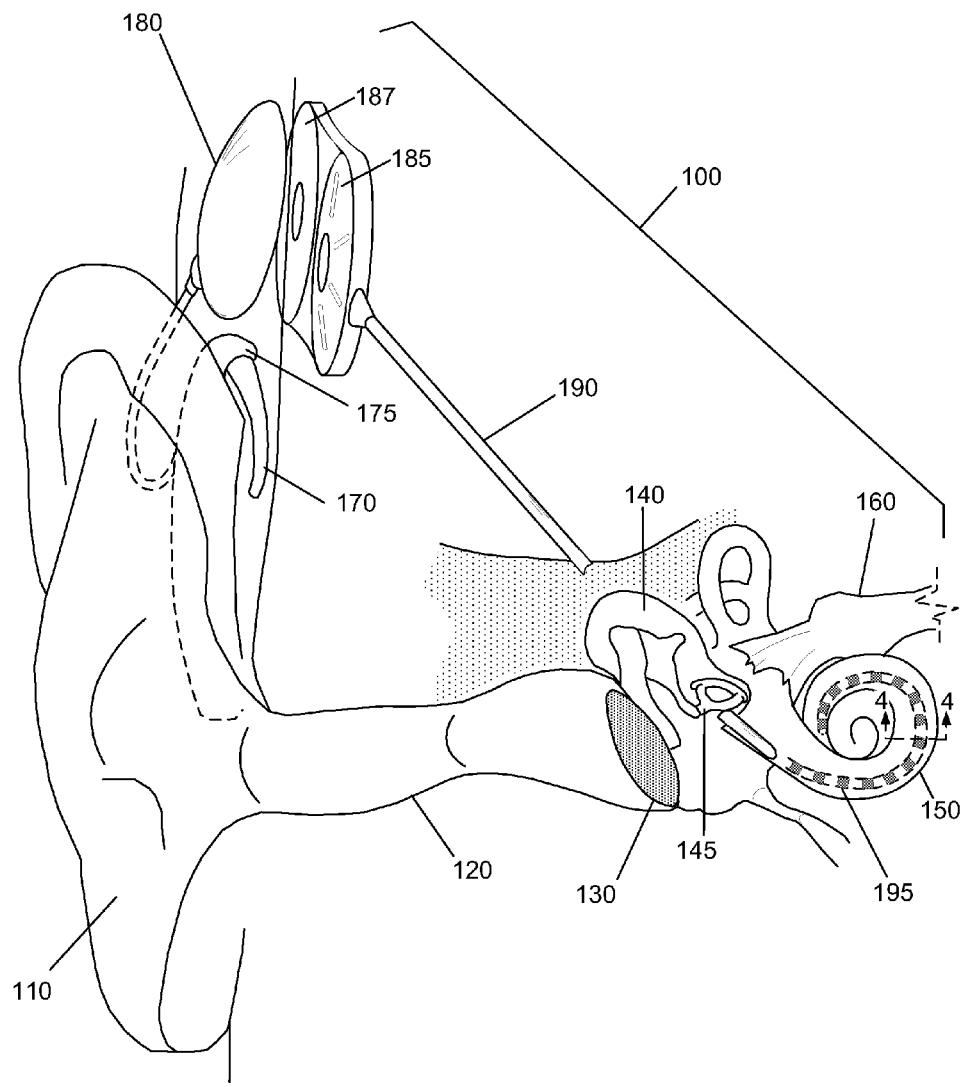
FIG. 1 is a diagram showing an illustrative cochlear implant system, according to one example of principles described herein.

A cochlear prosthesis may be used to restore a sense of hearing in a patient by directly stimulating nerve cells in the cochlea. The cochlear prosthesis includes an electrode array which is inserted into the cochlea. The electrode array typically includes a linear array of electrodes along the length of a flexible body. The electrode array is pushed into the cochlea through a cochleostomy. As the electrode array contacts the internal walls of the cochlea, the flexible body bends and conforms to the shape of cochlea. However, the contact between the flexible body and the tissues within the cochlea can cause trauma to the cochlea which leads to the loss of residual hearing.

This specification describes a steerable stylet that allows for automated insertion of the electrode array into the cochlea. The steerable stylet is inserted into a lumen within the electrode array. Sensors within the stylet detect contact with the cochlea wall and actuators respond by moving the electrode array away from the wall. The electrode array is then incrementally advanced into the cochlea and the process is repeated. Ideally, the electrode array can be maneuvered inside the cochlea so as to avoid or minimize contact with the walls of the cochlear lumen at all times. The force can be kept below a safe limit by moving the electrode array inside the cochlea in small increments so that, when contact occurs, it is very gentle. In this way, the electrode array can be advanced to a depth of 18 mm to 30 mm using minimal force. In some examples, the steerable stylet remains fully inserted within the lumen until the electrode array is in its desired location. In other examples, the electrode array is advanced off from the stylet during the insertion process.

The insertion process may be fully or partially automated. In a fully automated process, the surgeon exposes the cochlea and makes the cochleostomy. The electrode array and steerable stylet are positioned in the cochleostomy. The automated process then inserts the electrode array to a desired position within the cochlea and withdraws the steerable stylet, leaving the electrode array in place. In one illustrative partially automated process, the surgeon may hold the insertion device and manually advance the electrode array into the cochlea. The steerable stylet senses contact between the electrode array and cochlea walls and actively moves the electrode array away from the cochlea walls when contact occurs. The invention described herein can be used for other leads and catheters in addition to cochlear implants.

In the following description, for purposes of explanation, numerous specific details are set forth in order to provide a thorough understanding of the present systems and methods. It will be apparent, however, to one skilled in the art that the present apparatus, systems, and methods may be practiced without these specific details. Reference in the specification to "an embodiment," "an example," or similar language means that a particular feature, structure, or characteristic described in connection with the embodiment or example is included in at least that one embodiment, but not necessarily in other embodiments. The various instances of the phrase "in one embodiment" or similar phrases in various places in the specification are not necessarily all referring to the same embodiment.

FIG. 1 is a diagram showing one illustrative embodiment of a cochlear implant (100) that is surgically placed within the patient's auditory system. Ordinarily, sound enters the outer ear (110) and is directed into the auditory canal (120) where the sound wave vibrates the tympanic membrane (130). The motion of the tympanic membrane is amplified and transmitted through the ossicular chain (140) which consists of three bones in the middle ear. The third of the ossicles, the stapes, or stirrup, (145) contacts the outer surface of the cochlea (150) and causes movement of the fluid within the cochlea (150). Cochlear hair cells respond to the fluid-borne vibration in the cochlea (150) and trigger neural electrical signals that are conducted from the cochlea (150) to the auditory cortex by the auditory nerve (160).

As indicated above, the cochlear implant (100) is a surgically implanted electronic device that provides a sense of sound to a person who is profoundly deaf or severely hard of hearing. As also noted above, in many cases deafness is caused by the absence or destruction of the hair cells in the cochlea, i.e., sensorineural hearing loss. In the absence of properly functioning hair cells, there is no way auditory nerve impulses can be directly generated from ambient sound. Thus, conventional hearing aids which amplify external sound wave provide no benefit to persons suffering from complete sensorineural hearing loss.

Unlike hearing aids the cochlear implant (100) does not amplify sound, but works by directly stimulating the auditory nerve (160) with electrical impulses. Consequently, providing a cochlear prosthesis typically involves the implantation of electrodes into the cochlea. The cochlear prosthesis operates by direct electrical stimulation of the auditory nerve cells, bypassing the defective cochlear hair cells that normally transduce acoustic energy into electrical energy. For persons with partial hearing loss, the cochlear implant can compensate for damage to defective portions of the cochlear mechanism, while allowing the patient to utilize any residual hearing provided by working portions of the cochlea.

External components of the cochlear implant include a microphone (170), speech processor (175), and transmitter (180). The microphone (170) picks up sound from the environment and converts it into electrical impulses. The speech processor (175) selectively filters and manipulates the electrical impulses and sends the processed electrical signals through a cable to the transmitter (180). The transmitter (180) receives the processed electrical signals from the speech processor (175) and transmits them to the cochlear implant (100) by electromagnetic induction and/or by using radio frequencies.

In this example, the cochlear implant (100) includes an antenna (187) and an internal processor (185). The antenna (187) and internal processor (185) are secured beneath the user's skin, typically above and behind the external ear (110). The internal processor (185) includes electronic circuitry housed in a hermetically sealed enclosure. This electronic circuitry is connected by a hermetically sealed feedthrough to the antenna (187). The antenna (187) receives power and signals from the transmitter (180) via electromagnetic induction and/or radio frequency signals. The internal processor (185) processes the received signals and sends modified signals through a separate hermetic feedthrough to the cochlear lead (190) and electrode array (195). The electrode array (195) is inserted into the cochlea (150) and provides electrical stimulation to the auditory nerve (160).

The implant works by using the tonotopic organization of the cochlea. The cochlea is arranged tonotopically, also referred to as "frequency-to-place" mapping. The tonotopic structure of the cochlea enables human beings to hear a broad range of acoustic frequencies. The nerve cells sense progressively lower frequencies from the basal end of the cochlea to the apex. For normal hearing, the brain is presented with the electrical signals from the different regions of the cochlea and, because of the tonotopic configuration of the cochlea, is able to discern the acoustic frequencies being heard. A cochlear implant simulates with its electrode contacts along the length of the cochlea to mimic this process.

Figure 2:
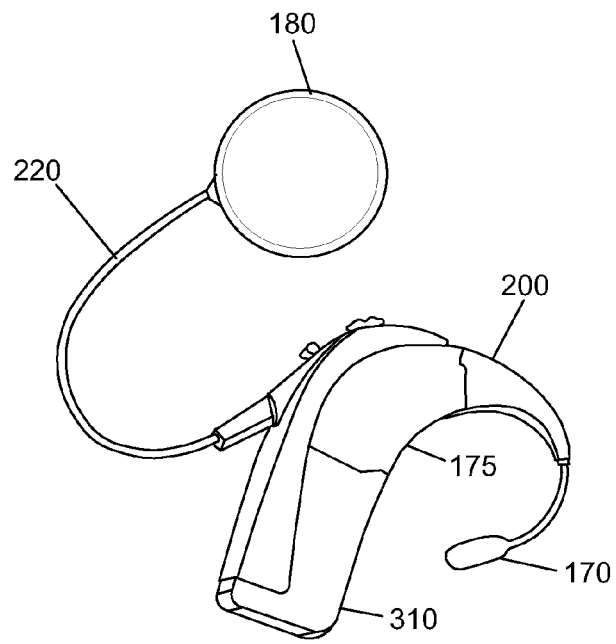
FIG. 2 is a diagram showing the external components of an illustrative cochlear implant system, according to one example of principles described herein.

FIG. 2 shows one illustrative embodiment of the external components of the cochlear implant. The microphone (170) is attached to the ear hook (200). The ear hook (200) secures the external components behind the outer ear. The microphone (170) senses environmental sounds and converts those sounds into electrical impulses. The processor (175) filters and manipulates the electrical impulses it receives from the microphone (170) and transmits processed electrical sound signals along the external cable (220) to the transmitter (180). The processor (175), microphone (170) and transmitter (180) are powered by a battery (310).

Figure 3:
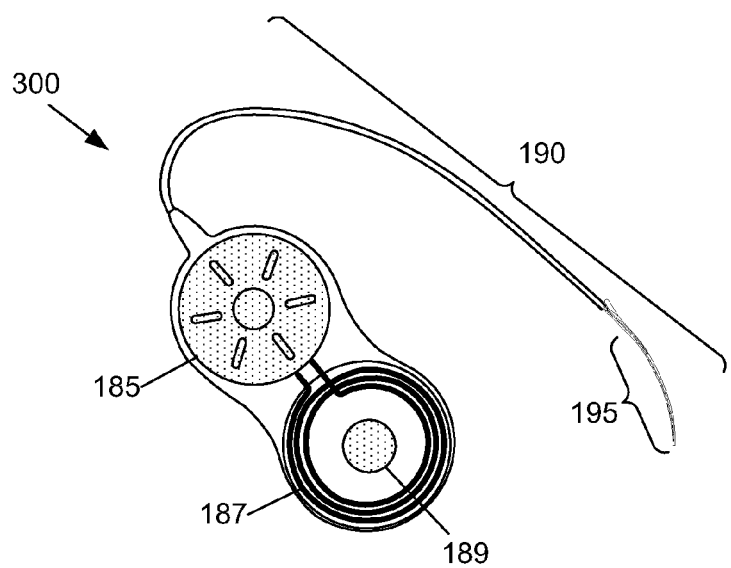
FIG. 3 is a diagram showing implanted components of an illustrative cochlear implant system, according to one example of principles described herein.

FIG. 3 shows one illustrative embodiment of the internal components of the cochlear implant device. As described above, the antenna (187) is connected to the internal processor (185). According to one embodiment, the antenna (187) is a coiled wire or wires that are encapsulated by a silicone overmold. A cavity within the center portion of the antenna (187) is adapted to receive a magnet (189). The transmitter (180, FIG. 2) is held in place externally over the antenna (187) by magnetic interaction between components within the transmitter (180, FIG. 2) and the implanted antenna magnet (189). The internal processor (185) is electrically connected to the antenna (187) and receives signals and power via the antenna (187). The internal processor (185) is connected to the cochlear lead (190) that terminates in a flexible end that contains the electrode array (195). The electrode array (195) consists of a plurality of individual electrode contacts made from platinum or a similar inert conductive material. These electrodes and associated wires are supported and connected by a flexible and durable biocompatible material, typically silicone rubber.

Figure 4A:
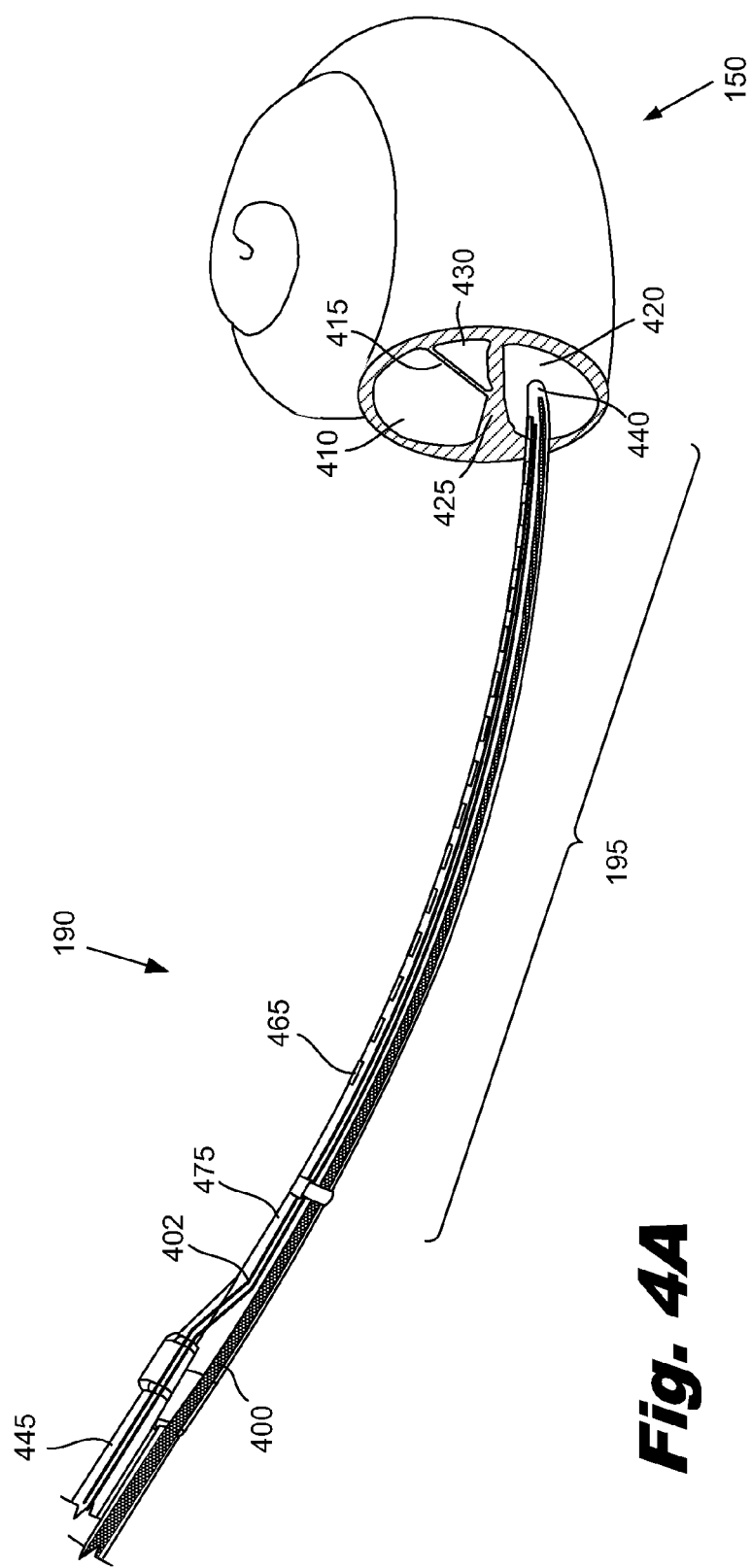
FIG. 4A is a diagram of an electrode array being inserted into a cochlea, according to one example of principles described herein.

FIG. 4A is a partially cutaway perspective view of a cochlea (150) and shows an illustrative electrode array (195) being inserted into the cochlea (150). The primary structure of the cochlea is a hollow, helically coiled, tubular bone, similar to a nautilus shell. The coiled tube is divided through most of its length into three fluid-filled spaces (scalae). The scala vestibuli (410) is partitioned from the scala media (430) by Reissner's membrane (415) and lies superior to it. The scala tympani (420) is partitioned from the scala media (430) by the basilar membrane (425) and lies inferior to it. A typical human cochlea includes approximately two and a half helical turns of its constituent channels. The electrode array (195) is inserted into one of the scalae, typically the scala tympani (420), to bring the individual electrodes into close proximity with the tonotopically organized nerves.

The illustrative cochlear lead (190) includes a lead body (445). The lead body (445) connects the electrode array (195) to the internal processor (185, FIG. 3). A number of wires pass through the lead body (445) to bring electrical signals from the internal processor (185, FIG. 3) to the electrode array (195). The wires that conduct the electrical signals generated by the processor are connected to the electrodes (465) within the electrode array (195). For example, electrical signals which correspond to a low frequency sound may be communicated via a first wire to an electrode near the tip (440) of the electrode array (195). Electrical signals which correspond to a high frequency sound may be communicated by a second wire to an electrode (465) near the proximal end of the electrode array (195).

According to one illustrative embodiment, the signal wires (402) and portions of the electrodes (465) are encased in a flexible body (475). The flexible body (475) may be formed from a variety of biocompatible materials including, but not limited to, medical grade silicone rubber. The flexible body (475) secures and protects the wires and electrodes (465). The flexible body (475) allows the electrode array (195) to bend and conform to the geometry of the cochlea. When placed within the cochlea (150), the electrode array (195) is positioned adjacent the lateral or outside wall of the scala tympani (420) and brings the individual electrodes into close proximity with the tonotopically organized nerves in the cochlea (150).

The lead (190) may also include a lumen which is adapted to receive a steerable stylet (400). The steerable stylet and lumen may pass through a substantial portion of the lead (190) to provide control of the electrode array (195) during insertion.

Figure 4B:
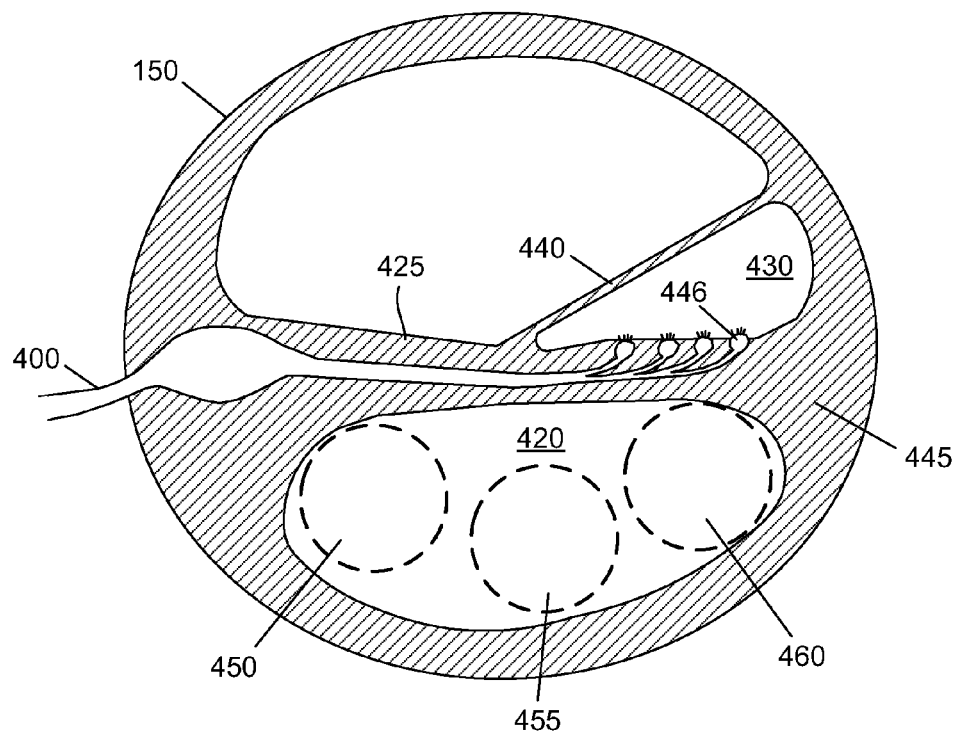
FIG. 4B is a cross sectional diagram of an electrode array within a cochlea, according to one example of principles described herein.

FIG. 4B is a cross sectional diagram of a cochlea (150) with an electrode array inserted into the scala tympani (420). The various cross sectional positions of electrode array within a cochlea (150) are represented by the dashed circles (450, 455, 460). In a first position (450) the electrode array is in contact with a medial wall of the scala tympani (420) and proximal to the cochlear nerve (400). This position can be a desirable final position for the electrode array because the electrical fields generated by the electrodes more easily trigger nerve impulses in the spiral ganglion (400). However, during insertion contact between the electrode array and the medial wall can be undesirable.

A second position (460) of the electrode array is against the spiral ligament (445) and basilar membrane (425). Injury or irritation of the basilar membrane (425) can damage the hair cells (446) which sense vibrations in the fluid filled channel and trigger nerve impulses. If the patient has residual hearing, injury to the basilar membrane and hair cells can result in a permanent reduction of this residual hearing.

In the center position (455) the electrode array is not in contact with any of the walls of the scala tympani. If the entire length of the electrode array does not contact the walls of the scala tympani, the insertion of the electrode array will be substantially frictionless and will not disturb the surrounding tissues.

FIGS. 5A and 5B are perspective views of an illustrative lead (190) with a steerable stylet (400) inserted into a lumen (505) in the lead. FIG. 5A shows a partially cut away view of the lead (190). Extending out of the cross section of the lead (190) is the steerable stylet (400) which is also cut away to show its component parts. A number of signal wires (402) are also shown in the cross section. The signal wires (402) are attached to the electrodes (465) and conduct electrical signals from the processor to the electrodes.

The cochlea has a variable radius of curvature that decreases from its base to its apex. When the stylet is at the base of the cochlea, its free end must assume a larger radius of curvature than when it is close to the apex. In order for the electrode array (195) to assume the shape of the cochlea when the pull wires are pulled, the cross section of the electrode array (195) is designed to vary along its length, tapering toward the distal end. In some embodiments, the electrode array (195) may be preformed in a helical shape having a radius that is tighter than the radius of the modiolus of the cochlea to be implanted. Tension on one or more of the wires straightens the electrode array (195). During the insertion the tension of the wires is controlled to move the electrode array (195) so that undesirable contact between the electrode array (195) and walls of the scala tympani are minimized.

FIG. 5B shows additional details of the lead lumen (505) and steerable stylet (400). The steerable stylet (400) includes a multi-lumen tube (510). A plurality of pull wires (515) and a sensor shaft (520) pass through the lumens in the multi-lumen tube (510).

FIG. 6A is a cross sectional diagram of an illustrative multi-lumen tube (510). The multi-lumen tube (510) may have a variety of configurations and sizes. In this example, the multi-lumen tube (510) includes a central sensor lumen (511) which is surrounded by four equally spaced wire lumens (512). The overall diameter of the multi-lumen tube (510) is approximately 330 microns with the central sensor lumen having a diameter of approximately 125 microns and the wire lumens having a diameter of approximately 50 microns. Accordingly, a pull wire has a diameter of less than 50 microns. In other embodiments, the sizes of the multi-lumen tube, sensor lumen, and wire lumens could vary. For example, the multi-lumen tube could have a diameter in the range of 200 to 500 microns, the sensor lumen could have a diameter in the range of 75 to 175 microns, and the wire lumens could have a diameter in the range of 35 to 75 microns.

The multi-lumen tube (510) may be formed from a variety of materials including, but not limited to silicone, fluoropolymers, polyurethane, or other materials. The multi-lumen tube (510) may be formed by casting, extrusion, or other appropriate methods. Depending on the material and the forming process, the walls which divide the lumens (511, 512) in the tube (510) may be as thin as 12.5 microns. In some embodiments, the outer surface of the multi-lumen tube (510) may be coated with parylene or other dry lubricant. This allows the multi-lumen tube (510) to be more easily inserted and withdrawn from the lumen of the lead. The wire lumens (512) may also be coated with lubricant to allow the pull wires to slide in the wire lumens (512) during actuation.

FIG. 6B is a cross sectional view of a steerable stylet (400) taken along the length of the stylet. A pull wire (515) is inserted into one of the wire lumens (512). The pull wire (515) may be formed from a variety of materials, including platinum iridium, stainless steel, silicon, carbon, aramid, or other suitable material. According to one illustrative embodiment, the pull wire (515) may be formed from platinum iridium and have a diameter of approximately 38 microns. Where the electrode array is preformed with a radius of curvature which is tighter than the curvature of the cochlea, the pull wires can be tensioned to straighten the electrode array during insertion. In one example, the maximum force on the wires is less than 0.5 Newtons. The length of the stroke on the pull wires to straighten the electrode array is less than 1 millimeter. In other applications or designs the wire diameter, force, and stroke may be different.

A wire anchor (516) is formed on one end of the pull wire (515). According to one example, the wire anchor (516) may be formed by inserting the wire into the wire lumen (512) and then placing the portion of the wire extending from the multi-lumen tube (510) in a flame. This melts the exposed metal and forms a ball on the end of the wire. This ball can then be staked in place using a silicone seal (530). In addition to securing the ends of the wires in place, the silicone seal (530) may serve a number of purposes, including sealing the end of the sensor lumen (511). A variety of other methods can be used to secure the terminal end of the wire (515). For example, the wire (515) may simply terminate within the silicone seal (530). Alternatively a clamp may be placed over the end of the wire and then sealed in place. The opposite end of the wire (515) is formed into an attachment loop (517). An actuator attachment (540) connects to the attachment loop (517). The actuator attachment (540) is driven by one or more actuators to control the extension and retraction of the pull wire (515). For clarity, FIG. 6B shows only one pull wire (515). However, other pull wires could be inserted into the wire lumens (512) as described above.

The active stylet (400) may be designed to have stiffness comparable to the stiffness of the passive stylets currently in use, or may be more or less stiff. The radius of curvature assumed by the stylet under the force exerted by the pull wires is directly related to the flexural rigidity of the stylet. The flexural rigidity, defined as the product of the area moment of inertia of the cross section of the stylet times its modulus of elasticity, is a measure of the stiffness of the stylet. The stiffer the stylet, the larger its flexural rigidity, and the larger the radius of curvature of the stylet under a given force applied by the pull wires. Therefore, for a given force applied through the pull wires, sections of the stylet that are less stiff than others will bend to a tighter radius of curvature than sections that are stiffer. Varying flexural rigidity along the axis of the stylet, with lower flexural rigidity at the distal end, provides better conformity to the tighter radius of curvature deeper into the cochlea.

Additional structural features may be built into the stylet to stiffen or soften it in particular directions so as to reduce the risk of unwanted buckling or twisting of the stylet. For example, the cross section of the stylet may be rectangular or square, ribs or trenches may be added or etched to increase the mechanical compliance in a particular direction, and the edges of the stylet may or may not be rounded to various degrees.

In some embodiments, a coil may be wound around the entire stylet structure. The coil, comprising 1 mil wire, maintains the pull wires close to the core, even when the stylet is bent to a tight radius. Upon activation of a pull wire, the coil transmits forces that bend the stylet. The coil and/or pull wires may be coated with parylene or other biocompatible coatings to prevent sticking to the coil or to the silicone encapsulant.

Many degrees of freedom are possible for controlling movement of the stylet. One or more pull wires deflect a distal portion of the stylet, and with it the electrode array, with respect to a proximal portion of the stylet. The entire stylet, along with the electrode array, can be moved in XYZ with respect to the patient, using the actuators or by hand. The stylet may also be rotated clockwise or counterclockwise with respect to the patient, either along with the lead or with respect to the lead while holding the lead fixed. Also, the stylet may be inserted or withdrawn with respect to the lead while holding the lead stationary or while moving the lead at a different rate or direction than the stylet.

Figure 7:
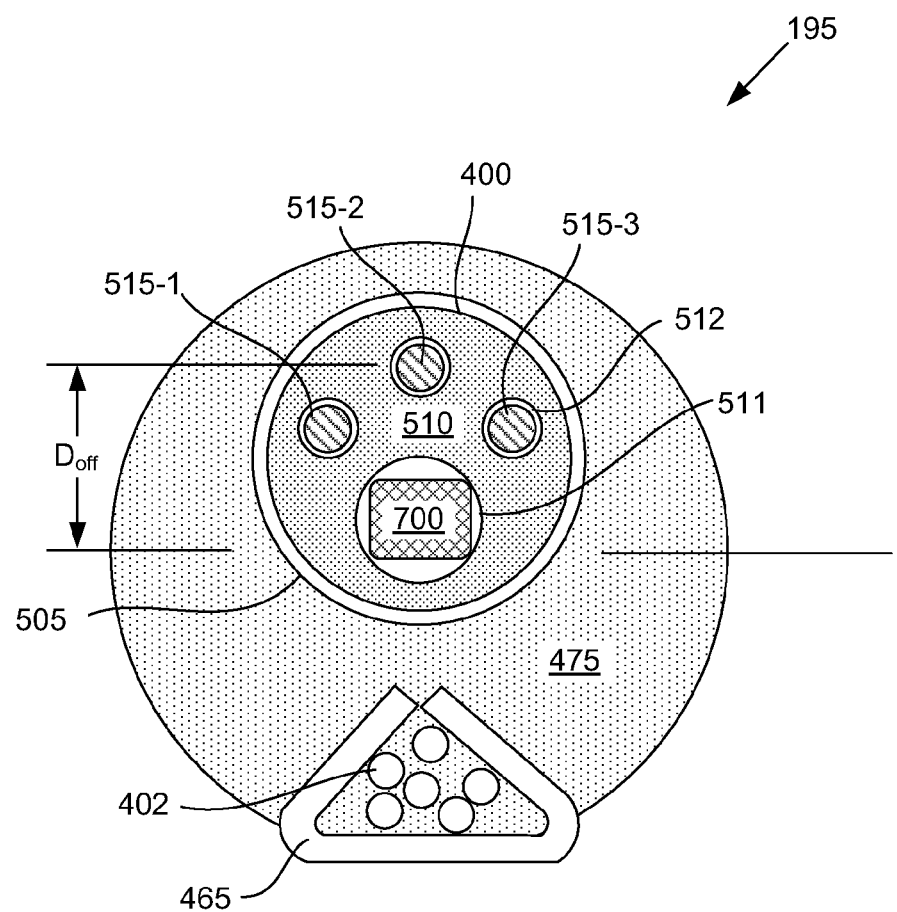
FIG. 7 is a cross sectional diagram of a steerable stylet inserted into an electrode array, according to one example of principles described herein.

FIG. 7 is a cross sectional diagram of a steerable stylet (400) inserted into the lead lumen (505) which is formed in the flexible body (475) of an electrode array (195). In this example, the steerable stylet (400) includes a multi-lumen tube (510) which has three wire lumens (512) and an offset sensor lumen (511). The sensor (700) is inserted into the sensor lumen (511) and the pull wires (515) are inserted into the wire lumens. The electrode array (195) also includes an electrode (465) and signal wires (402).

To straighten the electrode array (195), one or more of the pull wires (515) are tensioned. Because the pull wires (515) are offset from middle plane of the electrode array by an offset distance $D_{off}$, the tension in the wires creates a moment that alters the shape of the electrode array (195). In one embodiment, the wire to the left is called the inner pull wire (515-1) and the wire to the right is called the outer pull wire (515-3). The inner wire (515-1) and the outer wire (515-3) are pulled together to straighten the electrode array (195). The sum of their moments is responsible for the curling and straightening of the electrode array (195). The difference between their moments is responsible for moving the electrode array (195) along to the right or left.

In other embodiments, the locations of stylet (400) and pull wires (515) may be different than that illustrated in FIG. 7. For example, the pull wires (515) may be located both above and below the midline of the electrode array (195). The pull wires (515) could then be used to more actively control the curling of the electrode array (195) around the cochlea. In this configuration, forming the electrode array (195) into a pre-curled shape may not be necessary.

As discussed above, the shape of the scala tympani is not a simple arc. Rather, the scala tympani has a helically coiled shape. To follow the scala tympani, the steerable stylet controls the shape of the electrode array (195) as it is progressively inserted into the cochlea. Initially, the pull wires are tensioned to straighten the electrode array (195). The electrode array (195) is then inserted into the cochlea until the scala begins to turn. At this point the tension in the pull wires is slightly relaxed and the tip of the electrode array (195) begins to make a gradual curve. The scala begins to ascend as well as tighten its radius of curvature. To follow this path, the pull wires are progressively relaxed as the electrode array (195) is inserted deeper into the cochlea. To accommodate the upward angle of the scala, one of the pull wires is not relaxed as much as the other. This pulls the tip of electrode array (195) upward (or to the left as the electrode array (195) is oriented in FIG. 7).

According to one embodiment, the central pull wire (515-2) is called the dither wire. The nominal tension of the dither wire (515-2) is only great enough to remove the slack from the wire. Periodically additional tension is applied to the dither wire (515-2). This results in an extension of the tip of the electrode array (195). A sensor (700) measures the extension of the electrode array (195) which is produced by the additional tension applied to the dither wire (515-2). If the extension is clipped or attenuated by contact between the electrode array (195) and a wall of the scala tympani, the inner and outer wires (515-1, 515-3) are adjusted to pull the electrode array (195) away from the wall. The dithering action is again performed to determine if the corrective action was successful. This process is repeated throughout the insertion to avoid all but the lightest contact between the electrode array (195) and the walls of the cochlea. In some examples, dithering could also be performed using the inner and outer wires (515-1, 515-3) or some other combination of the three pull wires (515) to sense contact with the cochlea in other directions.

The wires illustrated in the figures have circular cross sections. However, the wires may have a variety of other configurations. For example, each pull wire may comprise multiple braided strands to increase strength while maintaining flexibility. For example, a braided silicon structure having 11 wires, each 15 μm in diameter would provide the strength of a single 50-μm wire but the stiffness of a 27 μm wire. Alternatively, a silicon wire ribbon, such as one having a cross section of 20 μm×40 μm, may be used for each pull wire.

FIGS. 8A through 12B describe various sensors which can be incorporated into a steerable stylet. FIGS. 8A and 8B are diagrams of an illustrative silicon strain gage (800). FIG. 8A is a plan view of the silicon strain gage (800) which includes contact pads (805), active region (810) and the terminal region (815). The silicon strain gage (800) may be fabricated using a number of techniques including lithographic and deposition techniques developed in the semiconductor industry. In this embodiment, the silicon strain gage (800) is configured to measure bending in two orthogonal directions. The illustrative silicon strain gage (800) has a width of 60 microns in the contact region (808) and a width of 20 microns in the active region (810). The length of the contact region (808) is approximately 400 microns and length of the active region is approximately 1500 microns. The terminal region has a length of approximately 100 microns. These dimensions are given only for purposes of illustration and show that this embodiment of the silicon strain gage (800) can be integrated with the other components of the illustrative steerable stylet. The silicon strain gage (800) may have a variety of different sizes and configurations and can be adapted to a wide range of applications.

FIG. 8B shows a cross section of the strain gage taken through the active portion (810) along line A-A. In this example, the strain gage (800) is formed on an n-type silicon substrate (835). Two active portions (825-1, 825-2) are formed on raised plateaus of the substrate (835). The active portions are p-doped silicon and run the length of the active region (810). An insulating layer (830) covers the substrate (835) and active portions (825) throughout the active region (810). According to one embodiment, the insulating layer (830) is formed from silicon oxide. The insulating layer (830) is removed in the contact and terminal regions (805, 815) to allow electrical connections to be made with the ends of the active portions (825). In this embodiment, an aluminum trace (820) connects to the ends of both the active portions (825) in the terminal region (815). The aluminum trace (820) is connected to a third contact pad (805-3). The first contact pad (805-1) connects to the proximal end of the first active portion (825-1) and the second contact pad (805-2) connects to the proximal end of the second active portion (825-2).

As strain is applied to the active portions (825) the resistance of the active portions (825) can change dramatically due to the piezoresistive effect. In semiconductors, the piezoresistive effect results from changes in the interatomic spacing which influences the conduction band of the material. This makes it easier or harder for the electrons to be raised into the conduction band and is manifest by a change in electrical resistance. Consequently, the active portions (825) exhibit substantial changes in electrical resistance which are proportional to the applied strain. These changes in resistance can be measured from the contact pads (805).

Figure 9:
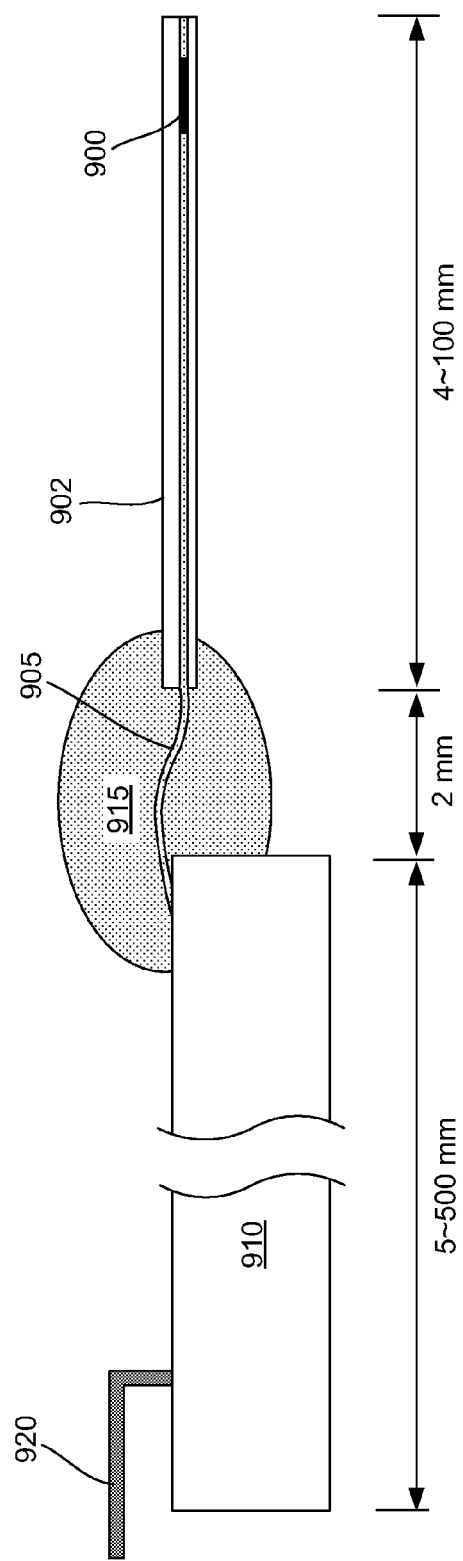
FIG. 9 is a diagram of an illustrative electrical connection to a sensor in a steerable stylet, according to one example of principles described herein.

FIG. 9 is a diagram of an illustrative electrical connection to a sensor in a sensor sleeve (902). According to one illustrative embodiment, the sensor sleeve (902) has a diameter of 100 microns or less and is slipped into the sensor lumen (511, FIG. 6A) in the steerable stylet (400, FIG. 6A). The sensor (900) may be any of a number of sensors, including the silicone strain gage described in FIGS. 8A and 8B. In this illustrative example, one or more gold wires (905) connect to the sensor (900) and pass out of the sensor sleeve (902). The end of the gold wire (905) is attached to a contact pad on a flex circuit (910). The section of the gold wire (905) which bridges the gap between the sensor sleeve (902) and the flex circuit (910) is supported by a flexible strain relief (915). The flexible strain relief (915) may be any of a number of materials including silicon rubbers, adhesives, and epoxies. According to one embodiment, the strain relief (915) is formed from Room Temperature Vulcanizing (RTV) silicone. The connection between the gold wire (905) and the flex circuit (910) can be formed in a variety of ways, including wedge or ball bonding techniques. Connector pins (920) provide electrical connections between detecting circuitry and the flex circuit (910).

A number of illustrative dimensions are shown in FIG. 9. For example, the length of the flex circuit may be approximately 5 to 500 millimeters, the gap between the flex circuit (910) and the sensor sleeve (902) may be approximately 2 millimeters, and the length of the sensor sleeve (902) may be approximately 4 to 100 millimeters in length. Depending on the sensor and the application, the interconnection between the sensor and the detecting circuitry may be significantly different than illustrated in FIG. 9.

Figure 10A:
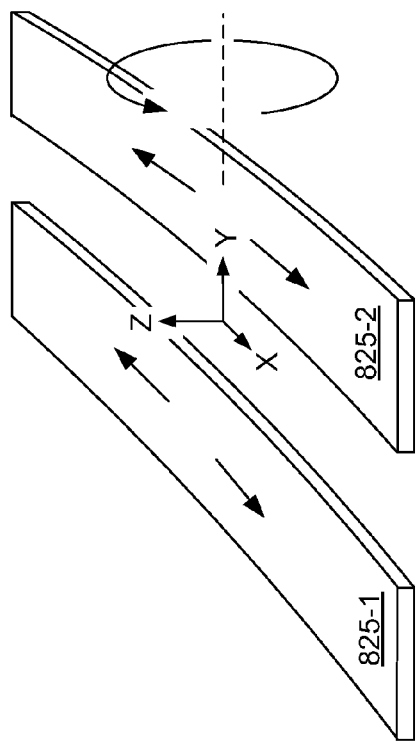
FIGS. 10A and 10B are diagrams showing principles of operation of an illustrative strain gage, according to one example of principles described herein.
Figure 10B:
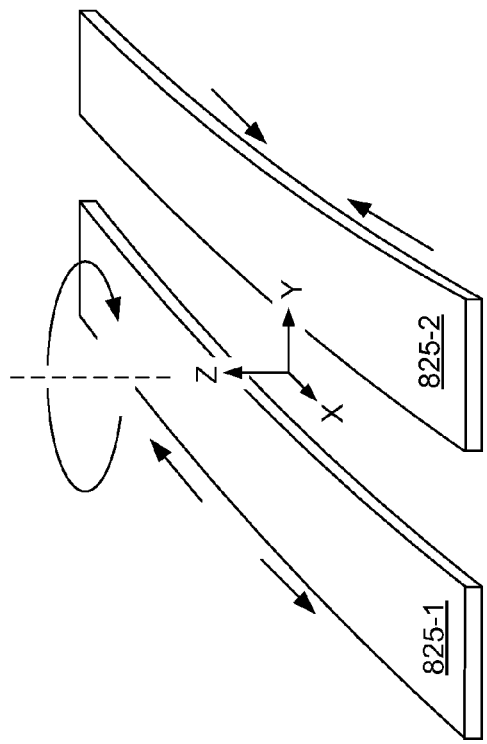

FIGS. 10A and 10B are diagrams showing principles of operation of the silicon strain gage (800) shown in FIGS. 8A and 8B. FIGS. 10A and 10B show only the two active portions (825) of the silicon strain gauge (800, FIG. 8B) and the bending moments acting on them. By comparing the sign and the magnitudes of the outputs from the two active portions (825) the bending of the silicon strain gage can be determined in two orthogonal directions: bending about the Y axis and bending about the Z axis.

FIG. 10A illustrates the active portions (825) bending upward as a result of a moment about the Y-axis. Because the bending is the same in both active portions (825), the resistance changes have the same sign and similar magnitudes. Consequently, the output from the two active portions can be summed to measure the applied moment and radius of curvature.

FIG. 10B shows the same active portions (825) with a moment applied about the Z-axis. In this case, the left active portion (825-1) is in tension and the right active portion (825-2) is in compression. One of the active portions will have an increase in resistance and the other active portion will have a decrease in resistance. Consequently, the difference between the outputs of the two active portions indicates the magnitude of the applied moment and the radius of curvature of the silicon strain gage.

Figure 11A:
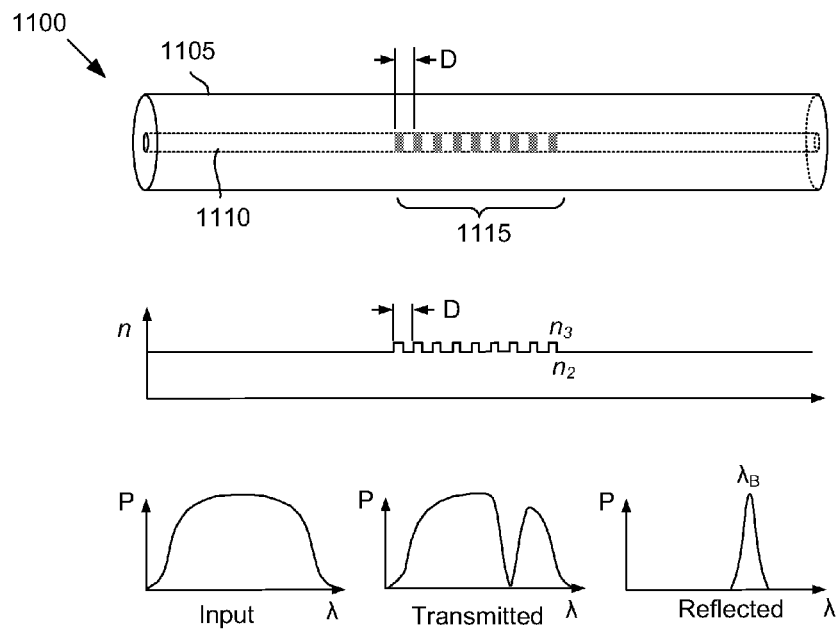
FIGS. 11A and 11B are diagrams of an illustrative Fiber Bragg sensor, according to one example of principles described herein.
Figure 11B:
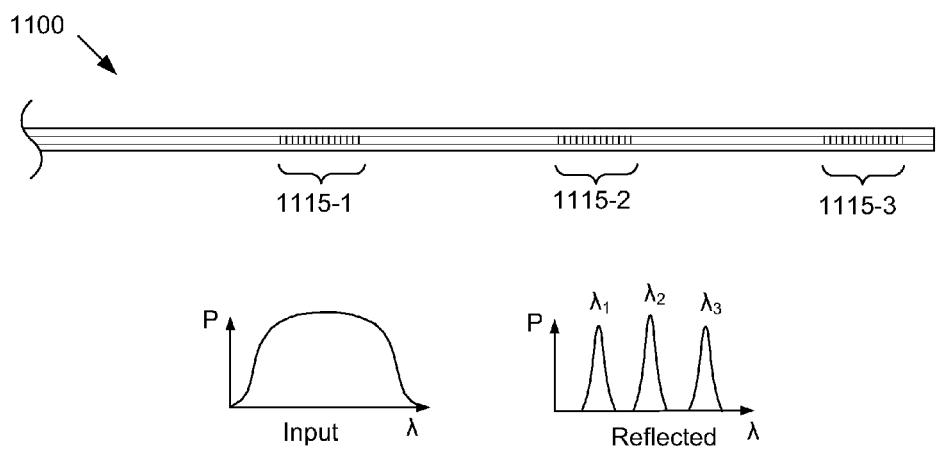

FIGS. 11A and 11B are diagrams of an illustrative fiber Bragg sensor (1100). The fiber Bragg sensor (1100) is a type of distributed Bragg reflector constructed in a segment of optical fiber that reflects particular wavelengths of light and transmits all others. This is achieved by adding a periodic variation to the refractive index of the fiber core, which generates a wavelength specific dielectric mirror.

FIG. 11A shows a segment of an illustrative fiber Bragg sensor (1100) that may be incorporated into a steerable stylet. The sensor includes an optical fiber made up of a core (1110) and cladding (1105). Differences in the index of refraction between the core and the cladding confines light passing through the fiber, with the majority of the light passing through the core. A fiber Bragg grating (1115) is formed in the core (1110). The fiber Bragg grating (1115) is made up of a number of periodically spaced variations in the optical index of the fiber. These variations in the optical index of the fiber can be formed in a variety of ways, including UV interference lithography, photomasks, and point-by-point laser techniques. The distance D between the variations is directly related to the wavelength of light which is reflected by the fiber Bragg grating (1115). Bending the fiber results in a change in the distance D and a corresponding shift in the wavelengths of light which are reflected by the grating (1115).

The graph below the segment of the fiber Bragg sensor (1100) shows the variation in the optical index along the core (1110). The optical index is plotted along the vertical axis of the graph and linear distance along the fiber is shown on the horizontal axis. As shown in the graph, the optical index in the core (1110) varies periodically between $n_2$ and $n_3$. FIG. 11A shows the grating lines as having uniform spacing. However a number of other grating types could be used. For example, chirped, tilted, superstructure, Gaussian apodized, discrete phase shift and other gratings could be used.

Three graphs along the bottom of FIG. 11A show, from left to right, the optical input to the sensor, transmitted light, and reflected light. In each of the graphs, the vertical axes show the intensity of light and the horizontal axes show the wavelengths of light. The first graph shows that a broad range of wavelengths are input into the fiber. The second graph shows that most of the input wavelengths are transmitted through the grating. The transmitted spectrum includes a dip which occurs around the grating reflection wavelength. The third graph shows the reflected spectrum. The reflected spectrum is centered on a grating reflection wavelength $\lambda_B$. As discussed above, $\lambda_B$ is determined by the distribution of the grating lines. The spacing between grating lines vary when the fiber is bent. The amount of shift in $\lambda_B$ is proportional to the radius of curvature of the fiber. Consequently, by sensing shifts in the grating reflection wavelength $\lambda_B$, the radius of curvature of the fiber can be determined.

FIG. 11B shows three Bragg gratings (1115) along an optical fiber (1100). Each of the Bragg gratings (1115) has a different grating spacing and consequently each of the gratings reflect different wavelengths of light. The two graphs at the bottom of FIG. 11B show the input spectrum and reflected spectrum. As described above, the vertical axes show the intensity of light and the horizontal axes show the wavelengths of light. The first graph shows that a broad range of wavelengths are input into the fiber. The second graph shows the reflected spectrum which has three distinct peaks: $\lambda_1$, $\lambda_2$, $\lambda_3$. Each of the peaks corresponds to one of the gratings (1115). By detecting shifts in the reflected peaks, the location and magnitude of bending along the fiber can be identified. This can be particularly useful when the optical fiber (1100) is incorporated into a steerable stylet which senses and controls the placement of an electrode array. The gratings (1115) that are distributed along the fiber provide information about the bending which occurs over length of the steerable stylet. For example, if the steerable stylet is kinked in a particular location, the fiber Bragg sensor can be used to sense the location and the radius of the kink. Additionally, the fiber Bragg sensor can provide feedback that allows appropriate control of the pull wires. This sensory feedback allows the steerable stylet to shape the electrode array during the insertion process.

Figure 12A:
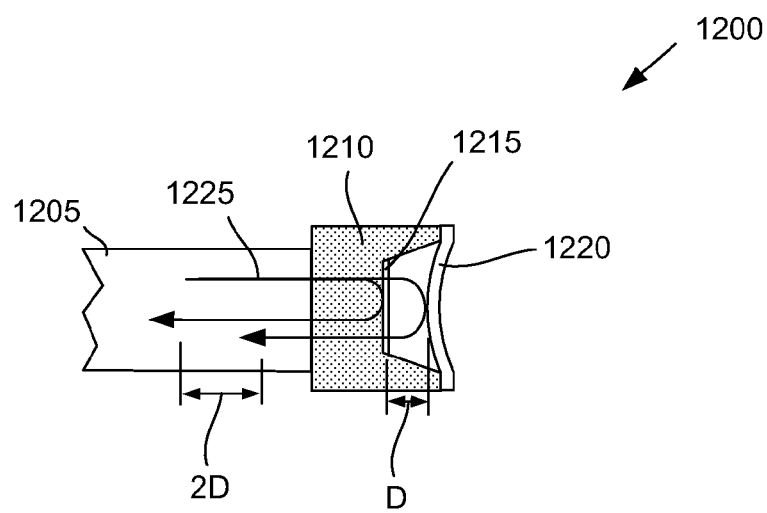
FIGS. 12A and 12B are diagrams of an illustrative fiber optic pressure sensor, according to one example of principles described herein.
Figure 12B:
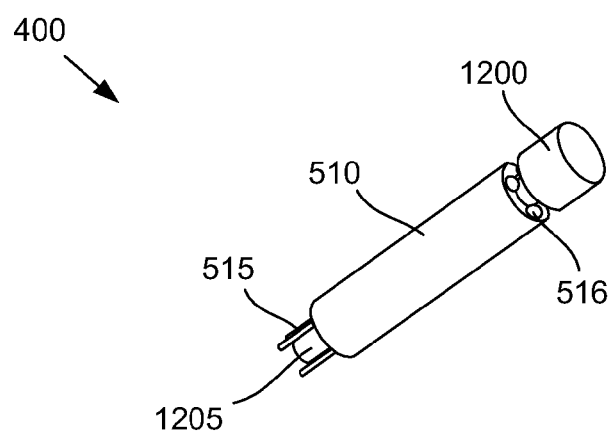

FIGS. 12A and 12B are diagrams of an illustrative fiber optic pressure sensor (1200). The pressure sensor (1200) is located on the terminal end of an optical fiber (1205). The pressure sensor (1200) includes a base (1210) which is optically and mechanically joined to the end of the optical fiber (1205). A dielectric mirror (1215) is placed on one surface of the base (1210). A second reflective surface is formed by a diaphragm (1220) which is attached to the base (1210) and deflects in response to external pressure. The dielectric mirror (1215) and the reflective surface of the diaphragm (1220) are spaced at a distance D which varies according to the external pressure applied to the sensor. These two reflective surfaces (1215, 1220) form a Fabry-Perot interferometer. A portion of the incoming optical energy (1225) is reflected by the dielectric mirror (1215) and another portion of the incoming optical energy is reflected by the inner surface of the diaphragm (1220). The difference in optical path length between the two reflected beams of light is 2D. The two reflected beams optically interfere and produce a characteristic interference pattern. By detecting changes in the interference pattern, the pressure applied to the diaphragm can be calculated.

FIG. 12B shows a Fabry-Perot pressure sensor (1200) which has been integrated onto the tip of a steerable stylet (400). The optical fiber (1205) passes through the center of the multi-lumen tube (510). Pull wires (515) also pass through lumens in the multi-lumen tube (510) and are terminated by wire anchors (516).

Figure 13:
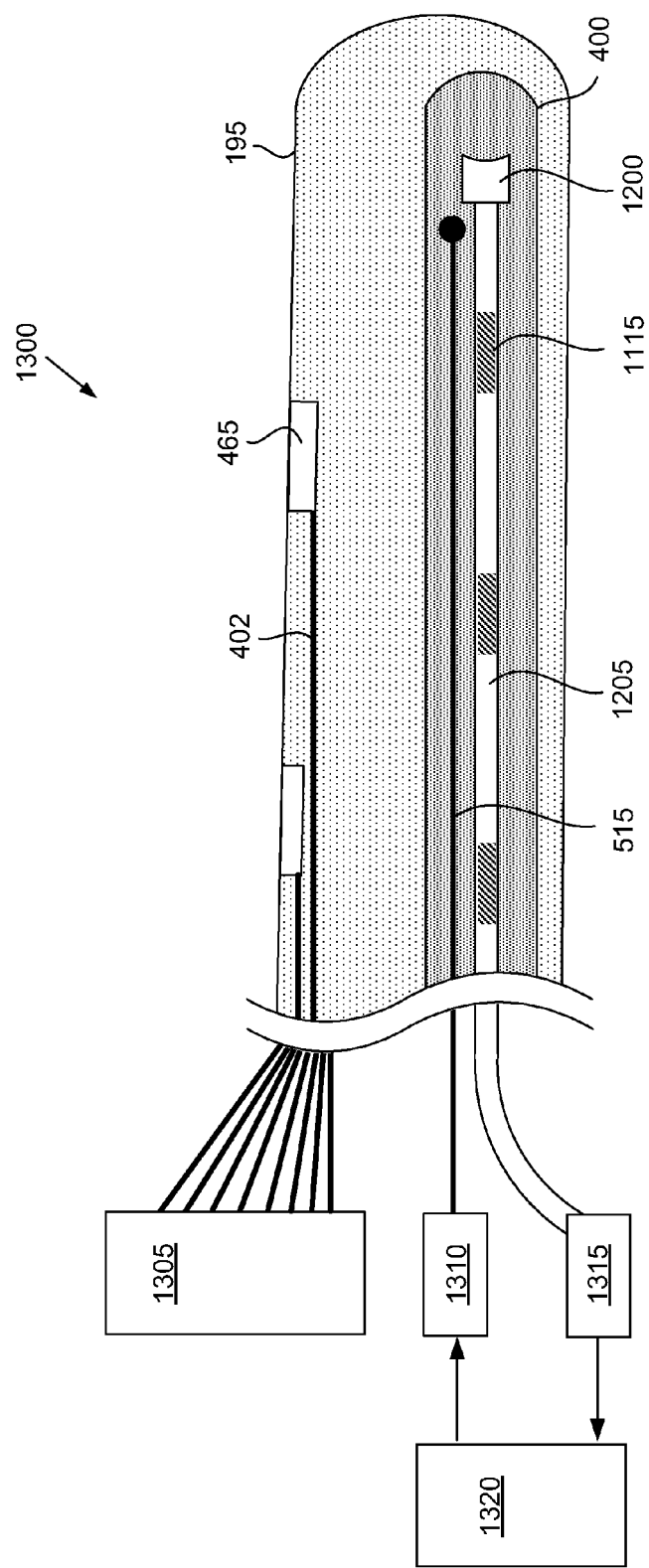
FIG. 13 is a cross sectional diagram of an electrode array with a steerable stylet and control circuits, according to one example of principles described herein.

FIG. 13 is a diagram of an illustrative cochlear lead implant system (1300). The implant system (1300) includes the electrode array (195) and a steerable stylet (400). As discussed above, the electrode array (195) includes a number of electrodes (465) which are electrically connected to a processor (1305) by signal wires (402). The steerable stylet (400) includes pull wires (515) which are connected to a pull wire actuator (1310). Although only one pull wire (515) is shown in this figure, a number of additional pull wires and associated actuators could be used. A number of sensors could also be included in the steerable stylet, including the silicon strain gage (800, FIG. 8A, 8B), fiber Bragg gratings (1115) and a fiber optic pressure sensor (1200). In this embodiment, the steerable stylet (400) includes three fiber Bragg gratings (1115) and a pressure sensor (1200) which are all integrated into the same optical fiber (1205).

These sensors are connected to a sensor support module (1315) which provides the necessary optical and electrical functions to make measurements from the sensors. For example, the sensor support module (1315) may generate an optical input spectrum and detect returned optical signals from the Bragg gratings (1115) and pressure sensor (1200).

A controller (1320) accepts the output from the sensor support module (1315) and makes appropriate adjustments during the implant process using actuators such as the pull wire actuator (1310). A number of other actuators may also be controlled by the controller (1320). For example, the controller (1320) may have a separate actuator that advances the electrode array (195) into the cochlea and an actuator that withdraws the steerable stylet (400) from the electrode array (195). The controller may also provide any number of other functions, such as visual or audio output, calibrations, or other functions. The cochlear lead implant system (1300) may operate in any of number of ways, including fully autonomous insertion or semi-autonomous insertion.

FIG. 13 is only one example of a steerable stylet (400) which could be used to control the shape of an electrode array (195). A variety of other configurations could be used. For example, the pressure and fiber Bragg gratings could be replaced with a variety of other sensors. In one embodiment, silicon strain gages could be distributed along the length of the stylet. A plurality of sensors could also be distributed in various radial positions in the stylet.

Additionally, the pull wires could be anchored at different longitudinal points along the steerable stylet to provide additional control over the shape of the steerable stylet. These additional pull wires may be provided at intermediate locations along the stylet between the proximal and distal end. Applying a force to one or more of these intermediate pull wires increases or decreases the radius of curvature of the stylet in the section proximal to the intermediate location without affecting the radius of curvature in distal of the intermediate connection point. The radius of curvature will be decreased if the intermediate pull wire is on the same side as the pull wire attached to the distal end, and will be increased if it is on the opposite side.

Figure 14:
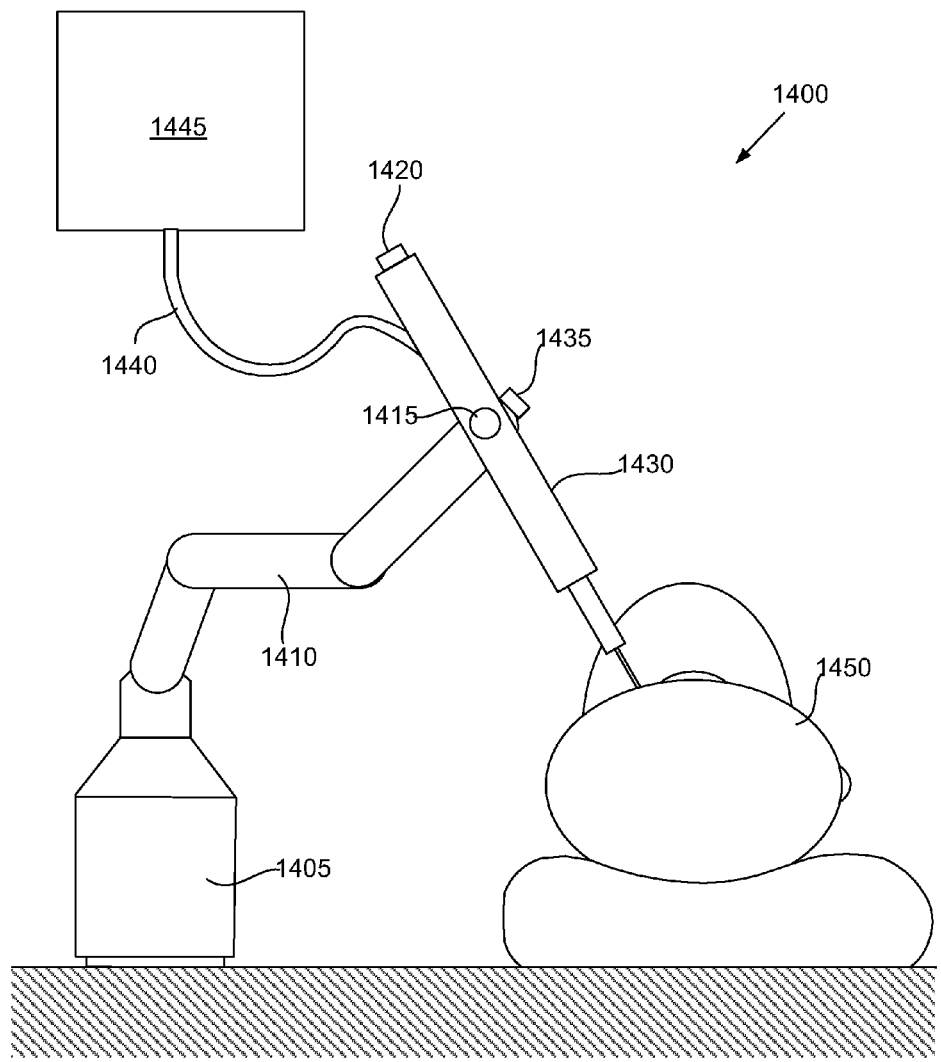
FIG. 14 is an illustrative diagram of automated insertion of the electrode array into a patient's cochlea, according to one example of principles described herein.

FIG. 14 is an illustrative diagram of a system (1400) for automated insertion of the electrode array into a patient's cochlea. The system (1400) includes an insertion tool (1430) which holds the cochlear lead and contains the actuators which manipulate the steerable stylet. In this embodiment, the insertion tool (1430) is supported by an articulated arm (1410) and base (1405). In other embodiments, the insertion tool (1430) may be held by the surgeon. The insertion tool (1430) is connected by a cable (1440) to a control unit (1445). As discussed above, the control unit (1445) may perform a number of functions, including sensor decoding and calibrations, output of status information, control of various actuators, and other functions.

To perform an automated insertion, the patient (1450) is first prepared for surgery and the necessary surgical openings are made to access the cochlea. A cochleostomy is performed to form an opening allowing access to the cochlea. The insertion tool (1430) and the attached cochlear lead are then appropriately positioned by the surgeon. The insertion tool (1430) includes a number of adjustment knobs (1415, 1420, 1435) which allow the surgeon to position the insertion tool (1430) appropriately prior to the automated insertion of the electrode array. For example, the insertion tool (1430) may be used to position the electrode array at the entrance to the oval window, perpendicular to the temporal bone. The positioning could be performed manually, via joystick, or by a computer vision system.

The automated system (1400) is then activated. The system inserts the electrode array into the cochlea to a desired location and then withdraws the steerable stylet.

Figure 15:
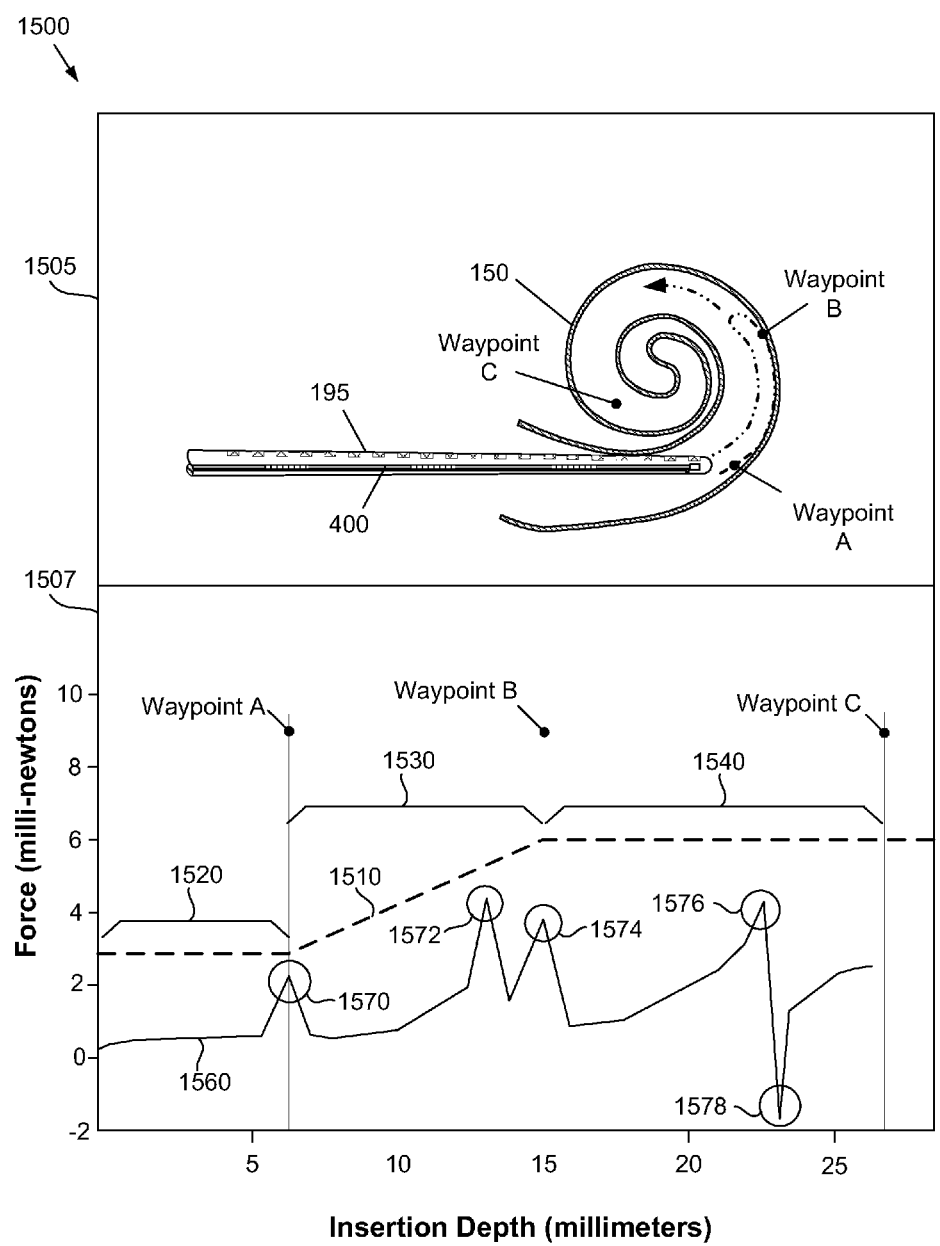
FIG. 15 is diagram which shows automated insertion of an electrode array into a patient's cochlea, according to one example of principles described herein.
Figure 16:
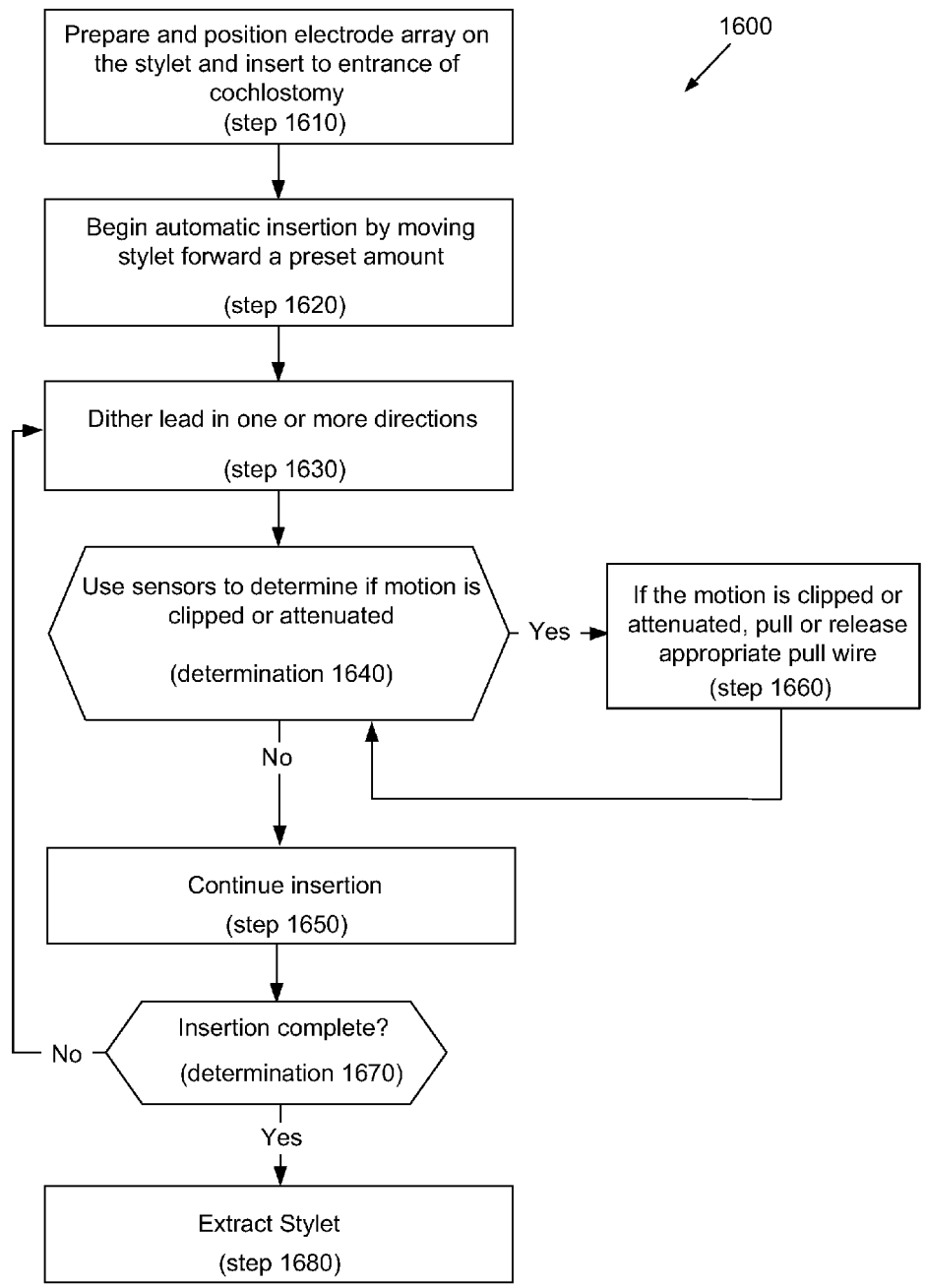
FIG. 16 is a flowchart that describes one illustrative method for automated insertion of an electrode array into a cochlea, according to one example of principles described herein.

FIGS. 15 and 16 describe the automated insertion of the electrode array into a patient's cochlea in more detail. FIG. 15 describes an insertion process where the steerable stylet contains a force sensor which measures the actual force of the electrode array against the wall of the cochlea. The sensor is sensitive to force of less than 1 micronewton, as shown in FIG. 15. Alternatively, the force sensor may be outside the electrode array but sense the forces applied by the electrode array on the cochlear wall. FIG. 15 shows an illustrative screenshot of a display (1500) which provides information throughout the automated electrode insertion procedure. The screenshot (1500) includes an upper window (1505) showing the current position of the cochlear electrode (190) within the cochlea and a lower window (1507) showing a force/insertion depth graph.

The current position of the electrode array (195) within the cochlea (150) could be determined in a number of ways including fluoroscopy, X-ray imaging, magnetic resonance imaging (MRI), or computerized axial tomography (CAT) scan image. Additionally or alternatively, measurements of the patient's cochlea could be made in advance. The position of electrode array (195) can then be estimated from sensors in the insertion tool and the steerable stylet. This estimated position could then be displayed in combination with the three dimensional model of the patient's cochlea.

A number of waypoints (waypoints A, B, and C) could be placed on the image to mark transition points during the cochlear insertion. By way of example and not limitation, waypoint A could be placed in a location corresponding to the initial contact of the tip of the electrode array (195) with the cochlear wall. Waypoint B could be placed at the point at which the tip of the electrode array (195) would be expected to leave the wall. Waypoint C could be placed at the final position of the electrode array tip when the electrode array (195) is correctly and fully inserted into the cochlea.

The lower window (1507) illustrates force in millinewtons as a function of insertion depth. The upper curve is a maximum allowable force profile (1510). For example, the maximum allowable force profile (810) may preclude the application of forces greater than 6 millinewtons. In most cases, this threshold is below the tactile perception of a surgeon. The illustrated maximum allowable force profile (1510) is a piecewise curve which is divided into 3 sections: a first section (1520) which represents the insertion of the electrode tip into the cochlea to waypoint A; a second section (1530) which represents a region of increasing allowable force as the tip continues around the first curve of the cochlea to waypoint B; and a final section (1540) which represents the allowable insertion force from waypoint B to the final position of the electrode array tip at waypoint C.

A second force curve (1560) is simulation of the actual force detected by the sensor in the steerable stylet during the current surgery. As illustrated by the actual force curve (1560), actual surgery profiles may have unique characteristics. In this example, the actual force remains close to zero during the initial insertion process. As the electrode array reaches waypoint A, the tip of the electrode array (195) contacts the cochlear wall, resulting in a peak (1570) in the force curve (1560). Corrective action is taken by relaxing the pull wires in the steerable stylet to allow the tip to curl. Insertion continues and produces relatively low forces for approximately 5 millimeters. However, the electrode array (195) again contacts the cochlear wall, producing a second peak (1572) in the force profile. Corrective action is again taken, but this time the corrective action fails to substantially reduce the force during the continued insertion. A third peak (1574) is generated. At this point, a third corrective action brings the electrode array (195) away from the cochlea wall. Gradually increasing forces are detected until an insertion depth of approximately 22 millimeters where the force again peaks (1576). The tip of the electrode array (195) is now deep within the cochlea and the scala tympani is narrower. When corrective action is taken, the electrode array (195) pulls away from the first wall and contacts an opposite wall. This results in a negative spike (1578) in the force curve (1560). The automated insertion system uses the positive spike (1576) and the negative spike (1578) to refine the corrective action and reduce the contact force for the remaining insertion. When the electrode array (195) reaches the target insertion depth of 27 millimeters, the steerable stylet is retracted from the lumen in the electrode array (195). This leaves the electrode array (195) in the desired position within the cochlea.

The profiles and other information contained within FIG. 15 are only illustrations. The actual screen, profiles, and limits may vary according to the design of the cochlear implant, electrode insertion system, methods of measurement, and individual characteristics of the patient. For example, the force profiles could be split into various vectors which better describe the forces applied to the tissues within the cochlea.

FIG. 16 is a flowchart that describes one illustrative method for automated insertion of an electrode array using position sensors in the steerable stylet for feedback. The electrode array is prepared by inserting the steerable stylet into the lumen and the electrode array is inserted through the surgical opening to the entrance of the cochleostomy (step 1610). The automatic insertion begins by moving the stylet forward a preset amount (step 1620). A first actuator in the steerable stylet is activated to dither the electrode array in one or more directions (step 1630). The position sensors are used to determine if the motion is clipped or attenuated by contact with the cochlear walls (determination 1640). For example, the output from the sensor within the stylet may be compared to anticipated output which correlates to the actuation. If the output is substantially similar to the anticipated output, no contact of the electrode array with a cochlear wall is detected; if the output is not substantially similar to the anticipated output, contact between the electrode array and the cochlear wall is detected. If the electrode array is close to the wall of the cochlea or to the basilar membrane, the pull wires are appropriately operated to bring the electrode array back into the middle of the cochlear lumen, where no contact is detected. Additionally or alternatively, the sensor response can be used to determine whether the sensor is closer to bony tissue or to the basilar membrane, the movement may be adjusted to keep the electrode array closer to the bone than to the basilar membrane.

If the position sensors do not sense attenuation of the dithering motion, the insertion continues (step 1650). If attenuation or clipping of the dithering motion of the electrode array is detected, the tension of one or more of the pull wires is adjusted to pull the electrode array away from the cochlear wall (step 1660). The process of dithering electrode array and detecting clipping or attenuation is then repeated.

A second determination is performed to determine if the insertion of the electrode array is complete (determination 1670). If the insertion is not complete, the process continues. If the insertion is complete, the steerable stylet is extracted from the lumen in the electrode array (step 1680) leaving the electrode array in position within the cochlea. The extraction sequence may be more or less critical, depending on insertion depth, the shape of a particular cochlea, and other factors. When the electrode array has reached its deepest position inside the cochlea, the pull wires are exerting a high force to maintain the stylet shaped for the tight radius of the cochlea. To minimize force of the electrode array against the cochlea as the stylet is withdrawn from the electrode array, the force on the pull wires is released in a controlled way during stylet extraction. According to one illustrative embodiment, the stylet is removed from the lumen by relaxing or releasing the pull wires and withdrawing the stylet. In other embodiments, the activation sequence of the actuators is recorded during insertion. This sequence is reversed during the withdrawal of the stylet. By mimicking the forces used during electrode array insertion, the stylet shape can be appropriately controlled at every point during withdrawal to minimize forces on the cochlear wall. By the time the distal portion of the stylet reaches the proximal portion of the electrode array, which is in the fairly straight proximal portion of the cochlea, the stylet should be substantially straight, and there should be no force exerted on the pull wires.

Alternatively, the device may be operated so that the stylet is inserted into the cochlea only partway to the electrode array's final depth, and then the soft silicone electrode array is pushed toward the apex of the cochlea without the support and guide of the stylet in the distal end of the electrode array. In this way, any contact forces of the electrode array against the walls of the cochlea towards the apex of the cochlea are kept to a minimum because of the softness of the unsupported electrode array. According to one embodiment, the insertion and extraction processes are performed in less than 90 seconds.

Using the method described above, one or more position sensors can be used to detect very light contacts between the electrode array and cochlea walls. The actuators in the steerable stylet compensate for contacts by conforming the electrode array to the shape of the cochlea. This method allows for automated insertion of the electrode array without prior three dimensional knowledge of the cochlea geometry. The system automatically adapts to irregularities within the cochlea.

Additionally, this technique could be used to map the internal spaces within the cochlea or other internal cavity. A map of the cochlea may be obtained as the sequence of locations occupied by the distal end of the stylet while it is being inserted. The location of the distal end of the stylet can be calculated using as input the force exerted by the pull wires and the knowledge of the stiffness of the stylet, since every combination of pull wire forces will deform the stylet in a unique predetermined way. This calculation is valid if no other forces act on the stylet, such as forces exerted by inside structures of the cochlea that are inadvertently contacted by the electrode array. Those additional forces could be approximately taken into account by including in the calculation measurements of the output of the sensors, or more specifically the deviation of the output of those sensors from their ideal output based solely on the forces of the pull wires. A map constructed in this way would be a single three-dimensional line that fits within the lumen of the scala tympani. To obtain additional information, one could measure the location of the walls of the cochlea using the sensors as proximity sensors. In this way one could obtain a three-dimensional map of the walls of the cochlea. This map may be useful to minimize contact with the cochlear walls during stylet extraction. Furthermore, this mapping technique can be used to map other cavities of the body, such as blood vessels.

In some embodiments, the response from sensors to the dithering motion can be used to determine if the electrode array is contacting a hard or soft surface. For example, if the electrode array contacts the hard wall of the cochlea, the electrode array will be deflected more than if the electrode array contacts the soft wall of the basilar membrane. The soft wall of the basilar membrane will deflect throughout the motion of the electrode array. Consequently, the output of the sensor during the dithering motion will be different when the electrode array contacts a hard surface verses a soft surface. By measuring the elasticity of contact, the sensors can differentiate whether the electrode array has contacted the endosteum lining the cochlea or the basilar membrane. The distance to the wall may be inferred from the length motion of the electrode array prior to deflection. In some embodiments, differentiation between endosteum and basilar membrane can be maximized by creating a custom stylet has an appropriate stiffness such that it is not much softer or much stiffer than the endosteum and the basilar membrane. This technique may be used to make an in-vivo assessment of the health of the basilar membrane, or it can be used at the end of the surgery to verify that the basilar membrane is still elastic and has not been ruptured by the surgical procedure.

The structures and methods described above can be used in many applications besides cochlear implants, and include multiple sensors of various types. Such sensors might include, for example, piezoresistive pressure sensors, temperature sensors (resistance changes with temperature), flow sensors (anemometry using a resistive heater and temperature sensor), magnetic field (loop printed wire onto silicon measures EMF created across the loop with a variable magnetic field), chemical (chemFET wherein the gate of the transistor is connected to fluid, measuring voltage changes to detect pH).

Variations of the illustrative structures may also be used. For example, in applications where steerability is not required, the pull wires can be eliminated, thus using a silicon core with integral sensors on it. As another variation, where steerability is important but sensing is not, the stylet may include one or more pull wires but no sensors.

In sum, the steerable stylet and insertion methods described above may have a number of advantages, including reduction in trauma to the cochlear tissues, decreased damage to electrode arrays during insertion, and improved patient outcomes. Additionally, the automated insertion decreases variation between insertions and can more precisely locate the electrode array within the cochlea.

The preceding description has been presented only to illustrate and describe embodiments and examples of the principles described. This description is not intended to be exhaustive or to limit these principles to any precise form disclosed. Many modifications and variations are possible in light of the above teaching.

What is claimed is:

1. A stylet for inserting an electrode array into a cochlea, comprising:
   a first sensor insertable within a lumen of the electrode array and sensitive to force applied by a lumen wall to the first sensor; and
   a first actuator adapted to move the electrode array in response to the force sensed by the first sensor, in which the first actuator comprises a plurality of pull wires and all pull wires are located in one half of a cross section orthogonal to a longitudinal axis of the stylet.

2. The stylet of claim 1, in which two of the pull wires can be used to reproduce the force applied to the electrode array by a third pull wire.

3. The stylet of claim 1, in which at least one pull wire must be tensioned for the electrode assembly to be straight.

4. A system for inserting a cochlear implant into the cochlea, the system comprising:
   a cochlear implant for implantation in a human being comprising:
      an electrode array and
      a longitudinal lumen;
   a steerable stylet removably insertable into the lumen of the cochlear implant, the stylet comprising:
      a plurality of longitudinal lumens;
      an actuator in a first stylet lumen; and
      a sensor and communication line in a second stylet lumen, where the sensor detects force applied by a wall of the second stylet lumen to the sensor and communicates an indication of the force through the communication line; and
   a controller controlling the actuator, the controller receiving communication from the sensor through the communication line.

5. The system of claim 4, wherein the controller dithers the actuator prior to advancing the electrode array.

* * * * *